US012018103B2

(12) United States Patent
George et al.

(10) Patent No.: US 12,018,103 B2
(45) Date of Patent: Jun. 25, 2024

(54) FLOW CELL AND METHODS

(71) Applicant: ILLUMINA CAMBRIDGE LIMITED, Cambridge (GB)

(72) Inventors: Wayne N. George, Ilford (GB); Andrew A. Brown, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 148 days.

(21) Appl. No.: 17/729,372

(22) Filed: Apr. 26, 2022

(65) Prior Publication Data

US 2022/0372182 A1 Nov. 24, 2022

Related U.S. Application Data

(60) Provisional application No. 63/182,370, filed on Apr. 30, 2021.

(51) Int. Cl.
*C09D 133/24* (2006.01)
*C08F 20/56* (2006.01)

(52) U.S. Cl.
CPC .................... *C08F 20/56* (2013.01)

(58) Field of Classification Search
CPC ..... C09D 133/24; C09D 133/26; B01L 3/502; B01L 3/5027; B01L 3/502707
See application file for complete search history.

(56) References Cited

U.S. PATENT DOCUMENTS

| 4,778,869 A | 10/1988 | Schirmann et al. |
| 6,258,454 B1 * | 7/2001 | Lefkowitz .............. B82Y 40/00 |
| | | 106/287.15 |
| 6,465,178 B2 | 10/2002 | Chappa et al. |
| 9,012,022 B2 * | 4/2015 | George ................ C12Q 1/6806 |
| | | 428/407 |

(Continued)

FOREIGN PATENT DOCUMENTS

| WO | 2016075204 A1 | 5/2016 |
| WO | 2020005503 A1 | 1/2020 |
| WO | WO-2020005503 A1 * | 1/2020 ............ C08F 212/10 |

OTHER PUBLICATIONS

Syed et al., "Next-generation sequencing library preparation: simultaneous fragmentation and tagging using in vitro transposition", Nature Methods 6, i-ii, Nov. 2009.

*Primary Examiner* — Robert C Boyle
(74) *Attorney, Agent, or Firm* — Dierker & Kavanaugh, P.C.

(57) ABSTRACT

An example of a flow cell includes a substrate and a pattern of two different silanes on at least a portion of a surface of the substrate. A first polymer is attached to a first of the two different silanes and a second polymer is attached to a second of the two different silanes. The first and second polymers respectively include a first functional group and a second functional group of a functional group pair, the functional group pair being selected from the group consisting of an activated ester functional group and an azide functional group, a tetrazine functional group and an acti- (Continued)

vated ester functional group, and a tetrazine functional group and an azide functional group. A first primer set is grafted to the first polymer and a second primer set is grafted to the second polymer. The first and second primer sets are different.

8 Claims, 6 Drawing Sheets

Specification includes a Sequence Listing.

(56) References Cited

U.S. PATENT DOCUMENTS

| | | | |
|---|---|---|---|
| 2015/0005447 A1* | 1/2015 | Berti | C08F 8/00 |
| | | | 427/302 |
| 2018/0179575 A1* | 6/2018 | George | C12Q 1/68 |
| 2018/0195950 A1* | 7/2018 | Tsay | B01L 3/502707 |
| 2019/0256633 A1 | 8/2019 | Gao et al. | |

* cited by examiner

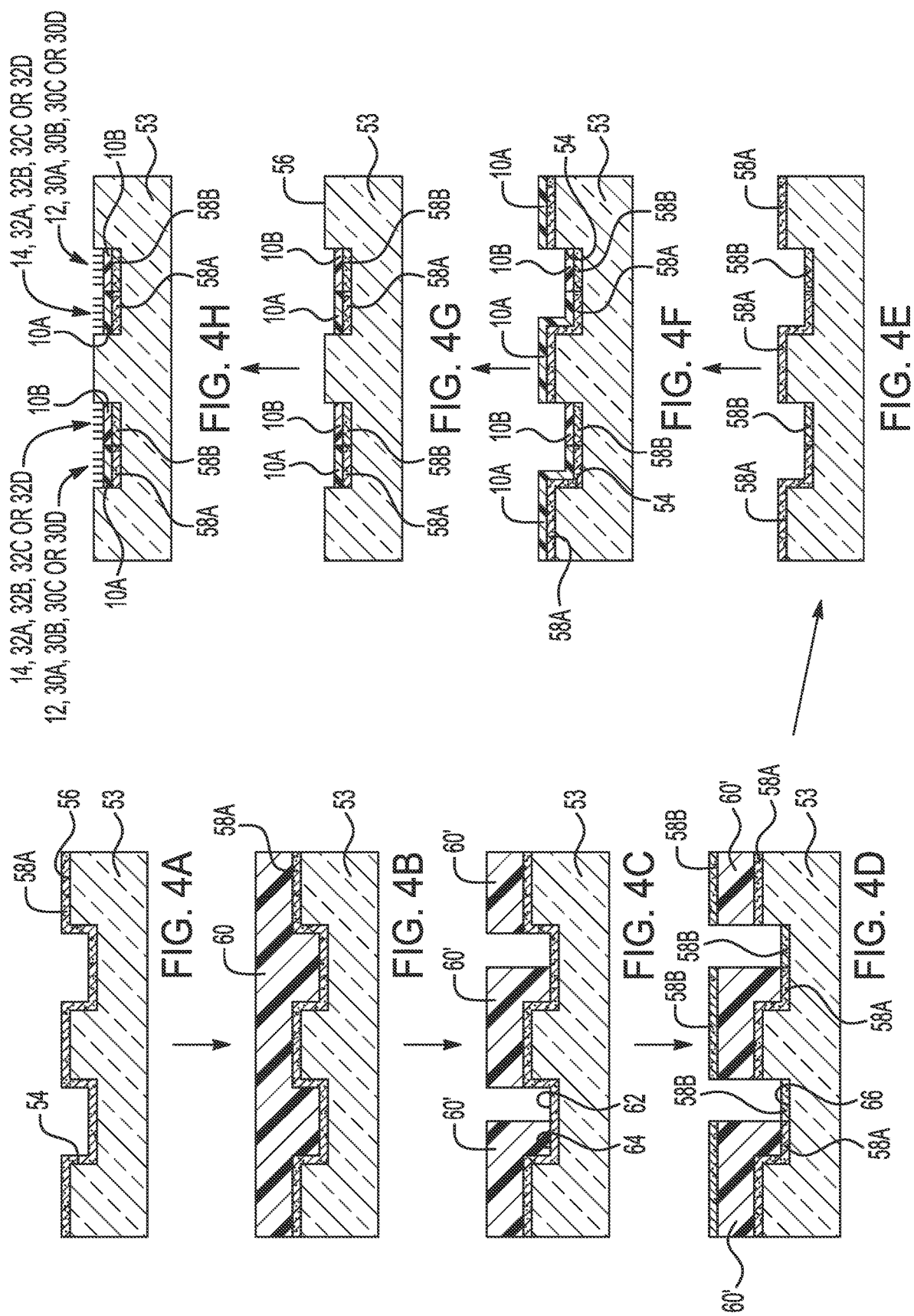

SEQUENCE LISTING

<160> NUMBER OF SEQ ID NOS: 14

<210> SEQ ID NO 1
<211> LENGTH: 28
<212> TYPE: DNA
<213> ORGANISM: Artificial Sequence
<220> FEATURE:
<223> OTHER INFORMATION: Synthesized

<400> SEQUENCE: 1
atgatacggc gaccaccgag auctacac                28

```
<210> SEQ ID NO 2
<211> LENGTH: 24
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(22)
<223> OTHER INFORMATION: 8-oxoguanine or uracil

<400> SEQUENCE: 2
caagcagaag acggcatacg anat                                          24

<210> SEQ ID NO 3
<211> LENGTH: 24
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(20)
<223> OTHER INFORMATION: 8-oxoguanine or uracil

<400> SEQUENCE: 3
caagcagaag acggcatacn agat                                          24

<210> SEQ ID NO 4
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (23)..(23)
<223> OTHER INFORMATION: allyl-T

<400> SEQUENCE: 4
aatgatacgg cgaccaccga ganctacac                                     29

<210> SEQ ID NO 5
<211> LENGTH: 35
<212> TYPE: DNA
<213> ORGANISM: Artificial Sequence
<220> FEATURE:
<223> OTHER INFORMATION: Synthesized

<400> SEQUENCE: 5
gctggcacgt ccgaacgctt cgttaatccg ttgag                              35

<210> SEQ ID NO 6
<211> LENGTH: 35
<212> TYPE: DNA
<213> ORGANISM: Artificial Sequence
<220> FEATURE:
<223> OTHER INFORMATION: Synthesized

<400> SEQUENCE: 6
ctcaacggat taacgaagcg ttcggacgtg ccagc                              35

<210> SEQ ID NO 7
<211> LENGTH: 35
<212> TYPE: DNA
<213> ORGANISM: Artificial Sequence
<220> FEATURE:
<223> OTHER INFORMATION: Synthesized
```

<400> SEQUENCE: 7
cgtcgtctgc catggcgctt cggtggatat gaact                              35

<210> SEQ ID NO 8
<211> LENGTH: 35
<212> TYPE: DNA
<213> ORGANISM: Artificial Sequence
<220> FEATURE:
<223> OTHER INFORMATION: Synthesized

<400> SEQUENCE: 8
agttcatatc caccgaagcg ccatggcaga cgacg                              35

<210> SEQ ID NO 9
<211> LENGTH: 35
<212> TYPE: DNA
<213> ORGANISM: Artificial Sequence
<220> FEATURE:
<223> OTHER INFORMATION: Synthesized

<400> SEQUENCE: 9
acggccgcta atatcaacgc gtcgaatccg caact                              35

<210> SEQ ID NO 10
<211> LENGTH: 35
<212> TYPE: DNA
<213> ORGANISM: Artificial Sequence
<220> FEATURE:
<223> OTHER INFORMATION: Synthesized

<400> SEQUENCE: 10
agttgcggat tcgacgcgtt gatattagcg gccgt                              35

<210> SEQ ID NO 11
<211> LENGTH: 34
<212> TYPE: DNA
<213> ORGANISM: Artificial Sequence
<220> FEATURE:
<223> OTHER INFORMATION: Synthesized

<400> SEQUENCE: 11
gccgcgttac gttagccgga ctattcgatg cagc                               34

<210> SEQ ID NO 12
<211> LENGTH: 34
<212> TYPE: DNA
<213> ORGANISM: Artificial Sequence
<220> FEATURE:
<223> OTHER INFORMATION: Synthesized

<400> SEQUENCE: 12
gctgcatcga atagtccggc taacgtaacg cggc                               34

<210> SEQ ID NO 13
<211> LENGTH: 24
<212> TYPE: DNA
<213> ORGANISM: Artificial Sequence
<220> FEATURE:
<223> OTHER INFORMATION: Synthesized

<400> SEQUENCE: 13
aggaggagga ggaggaggag gagg                                          24

<210> SEQ ID NO 14
<211> LENGTH: 24

```
<212> TYPE: DNA
<213> ORGANISM: Artificial Sequence
<220> FEATURE:
<223> OTHER INFORMATION: Synthesized

<400> SEQUENCE: 14
cctcctcctc ctcctcctcc tcct                                              24
```

FLOW CELL AND METHODS

CROSS REFERENCE TO RELATED APPLICATION

This application claims the benefit of U.S. Provisional Application Ser. No. 63/182,370, filed Apr. 30, 2021, the contents of which is incorporated by reference herein in its entirety.

REFERENCE TO SEQUENCE LISTING

The Sequence Listing submitted via EFS-Web is hereby incorporated by reference in its entirety. The name of the file is ILI214B_IP-2090-US_Sequence_Listing_ST25.txt, the size of the file is 3,010 bytes, and the date of creation of the file is Apr. 20, 2022.

BACKGROUND

Polymer or hydrogel-coated substrates are used in many technological applications. In one example, implantable medical devices can be coated with biologically inert polymers. In another example, a wound dressing may be coated with a thin hydrogel layer. In yet another example, polymer or hydrogel coated substrates may be used for the preparation and/or analysis of biological molecules. Some molecular analyses, such as certain nucleic acid sequencing methods, involve the attachment of nucleic acid strands to a polymer or hydrogel-coated surface of a substrate.

SUMMARY

Disclosed herein is a flow cell including a substrate and orthogonal polymers in a pattern across the substrate. As used herein, the term "orthogonal polymers" refers to two different polymers, each of which has different functional groups for attachment to the substrate and for attachment to a different primer set. Thus, the polymers have orthogonal functionality. In some instances, each polymer has a different type of functional group that is capable of both substrate and primer set attachment. In other instances, each polymer has at least two different types of functional groups, one of which is capable of substrate attachment and another of which is capable of primer set attachment. The orthogonality of polymers can be controlled during polymer synthesis, thus enabling the polymers to be designed for a particular flow cell application. Moreover, the orthogonality of polymers enables the different polymers to be applied simultaneously and in the desired pattern across the substrate. The simultaneous application may lead to a more streamlined workflow in flow cell manufacturing.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

Figure 6:
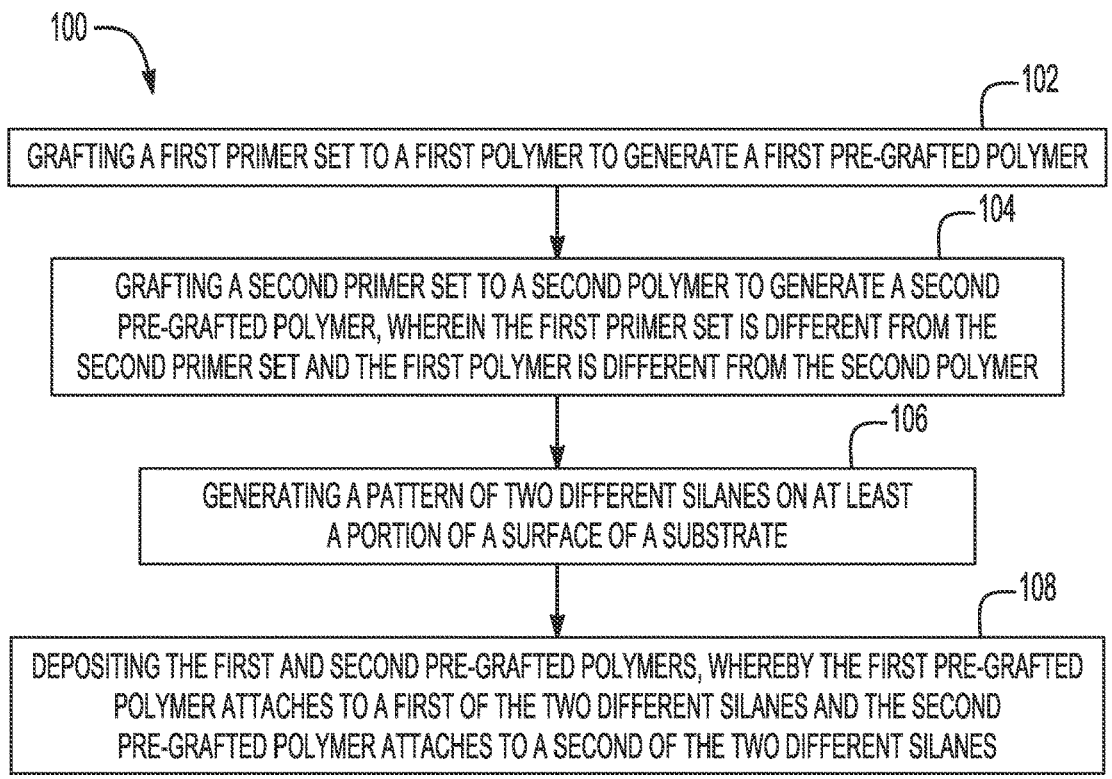
Figure 7:
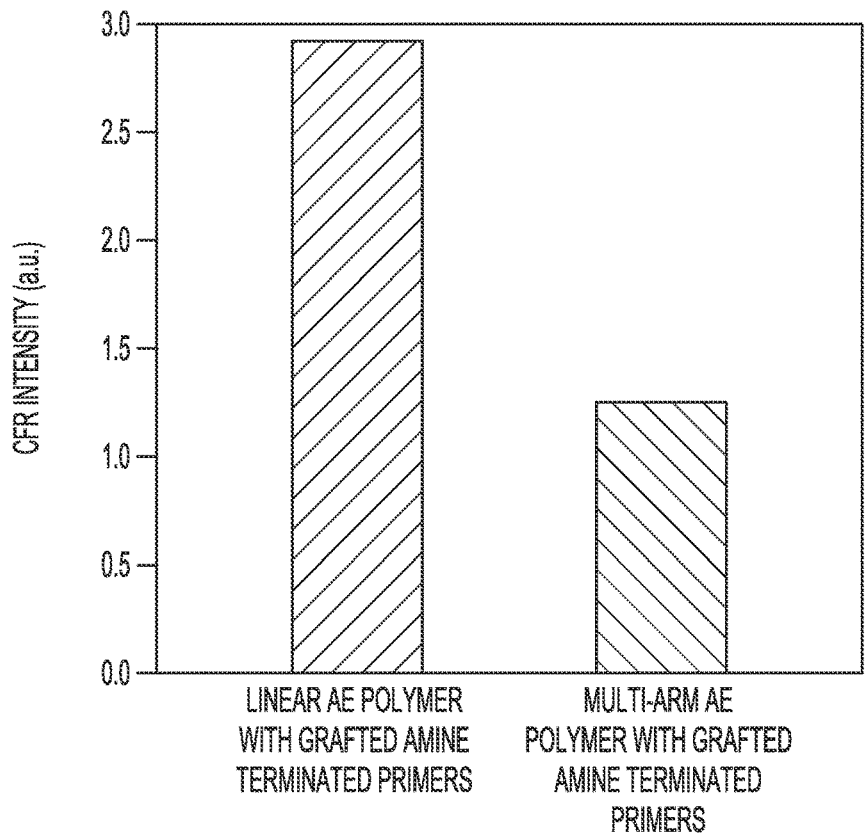

Each of FIG. 4A through FIG. 4H is a schematic diagram illustrating one or more processes involved in an example of a method for making an example of a flow cell disclosed herein;

Each of FIG. 5A through FIG. 5H is a schematic diagram illustrating one or more processes involved in another example of the method for making an example of the flow cell disclosed herein;

FIG. 6 is a flow diagram illustrating another example of the method for making an example of the flow cell disclosed herein; and FIG. 7 is a graph depicting the results of a Cal Fluor Red (CFR) assay using two example polymers disclosed herein.

DETAILED DESCRIPTION

Examples of the flow cell disclosed herein include orthogonal polymers patterned on a substrate surface. Orthogonal polymers have orthogonal functionality, e.g., different functional groups for attachment to the substrate surface and for attachment to different primer sets. The different substrate attachment mechanisms allow the polymers to be simultaneously applied and attached in a desired pattern on the substrate surface. The different primer set attachment mechanisms expand the sequencing capability of the flow cell as different primer sets are attached in different locations across the substrate surface. This can enable simultaneously paired end sequencing. Still further, the functionality of each polymer is controllable during its synthesis, which enables the final polymer to have multiple targeted and dialed in functionalities.

Definitions

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

The terms first, second, etc. also are not meant to imply a specific orientation or order, but rather are used to distinguish one component from another.

It is to be understood that the ranges provided herein include the stated range and any value or sub-range within the stated range, as if such values or sub-ranges were explicitly recited. For example, a range of about 400 nm to about 1 μm (1000 nm), should be interpreted to include not only the explicitly recited limits of about 400 nm to about 1 μm, but also to include individual values, such as about 708 nm, about 945.5 nm, etc., and sub-ranges, such as from about 425 nm to about 825 nm, from about 550 nm to about 940 nm, etc. Furthermore, when "about" and/or "substantially" are/is utilized to describe a value, they are meant to encompass minor variations (up to +/−10%) from the stated value.

An "acrylamide" is a functional group with the structure

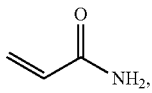

where each H may alternatively be an alkyl, an alkylamino, an alkylamido, an alkylthio, an aryl, a glycol, and optionally substituted variants thereof.

The term "activated ester" refers to an ester functional group that is highly susceptible toward nucleophilic attack.

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-C6 alkyl" indicates that there are one to six carbon atoms in the alkyl chain, i.e., the alkyl chain is selected from the group consisting of methyl, ethyl, propyl, iso-propyl, n-butyl, isobutyl, sec-butyl, t-butyl, pentyl, and hexyl.

As used herein, "alkylamino" refers to an alkyl group in which one or more of the hydrogen atoms are replaced by an amino group, where the amino group refers to an —NR$_a$R$_b$ group, where R$_a$ and R$_b$ are each independently selected from a C1-C6 alkyl, C2-C6 alkenyl, C2-C6 alkynyl, C3-C7 carbocycle, C6-C10 aryl, a 5-10 membered heteroaryl, and a 5-10 membered heterocycle.

As used herein, "alkylamido" refers to an alkyl group in which one or more of the hydrogen atoms are replaced by a C-amido group or an N-amido group. A "C-amido" group refers to a "—C(=O)N(R$_a$R$_b$)" group in which R$_a$ and R$_b$ can independently be selected from the group consisting of alkyl, alkenyl, alkynyl, cycloalkyl, cycloalkenyl, cycloalkynyl, aryl, heteroaryl, heteroalicycle, aralkyl, or (heteroalicyclic)alkyl. An "N-amido" group refers to a "RC(=O)N(R$_a$)—" group in which R and R$_a$ can independently be selected from the group consisting of alkyl, alkenyl, alkynyl, cycloalkyl, cycloalkenyl, cycloalkynyl, aryl, heteroaryl, heteroalicycle, aralkyl, or (heteroalicyclic)alkyl. Any alkylamido may be substituted or unsubstituted.

As used herein, "alkylthio" refers to RS—, in which R is an alkyl. The alkylthio can be substituted or unsubstituted.

As used herein, "alkene" or "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

The term "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl. Any aryl may be a heteroaryl, with at least one heteroatom, that is, an element other than carbon (e.g., nitrogen, oxygen, sulfur, etc.), in ring backbone.

As used herein, the term "attached" refers to the state of two things being joined, fastened, adhered, connected or bound to each other, either directly or indirectly. For example, a nucleic acid can be attached to a functionalized polymer by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to —N$_3$.

A "block copolymer" is a copolymer formed when two or more monomers cluster together and form blocks of repeating units. Each block may have at least one functional group which is/are not present in adjacent blocks. Specific examples of block copolymers will be described further below.

As used herein, "carbocycle" means a non-aromatic cyclic ring or ring system containing only carbon atoms in the ring system backbone. When the carbocycle is a ring system, two or more rings may be joined together in a fused, bridged or spiro-connected fashion. Carbocycles may have any degree of saturation, provided that at least one ring in a ring system is not aromatic. Thus, carbocycles include cycloalkyls, cycloalkenyls, and cycloalkynyls. The carbocycle group may have 3 to 20 carbon atoms. Examples of carbocycle rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl. Any of the carbocycles may be heterocycles, with at least one heteroatom in ring backbone.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). In some examples, cycloalkyl groups can contain 3 to 8 atoms in the ring(s). A cycloalkyl group may be unsubstituted or substituted. Example cycloalkyl groups include cyclopropyl, cyclobutyl, cyclopentyl, cyclohexyl, cycloheptyl, and cyclooctyl.

As used herein, "cycloalkenyl" or "cycloalkene" means a carbocycle ring or ring system having at least one double bond, wherein no ring in the ring system is aromatic. Examples include cyclohexenyl or cyclohexene and norbornenyl or norbornene.

As used herein, "cycloalkynyl" or "cycloalkyne" means a carbocycle ring or ring system having at least one triple bond, wherein no ring in the ring system is aromatic. An example is cyclooctyne. Another example is bicyclononyne. Still another example is dibenzocyclooctyne (DBCO).

"Dendritic agent," as used herein, refers to the center of a multi-branched polymer. The dendritic agent is a synthetic polymer with a branching, and in some instances treelike, structure. The dendritic agent can have anywhere from 2 arms (branches) to 30 arms. The dendritic agent includes a central molecule/compound and arms (or branches) that extend from the central molecule/compound, where each arm includes an initiator in each arm. For example, a dendritic RAFT agent includes a central molecule/compound and arms (or branches) that extend from the central molecule/compound, where each arm includes a thiocarbonylthio group at or near its end. In some examples, the dendritic RAFT agent has 2 arms (which is linear), 3 arms, 4 arms, 6 arms, or 8 arms.

The term "depositing," as used herein, refers to any suitable application technique, which may be manual or automated, and, in some instances, results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

As used herein, the term "depression" refers to a discrete concave feature in a patterned substrate or a patterned resin having a surface opening that is at least partially surrounded by interstitial region(s) of the substrate or the patterned resin. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or two interconnected wells. The depression may also have more complex architectures, such as ridges, step features, etc.

The term "each," when used in reference to a collection of items, is intended to identify an individual item in the collection, but does not necessarily refer to every item in the collection. Exceptions can occur if explicit disclosure or context clearly dictates otherwise.

As used herein, the term "flow cell" is intended to mean a vessel having a flow channel where a reaction can be carried out, an inlet for delivering reagent(s) to the flow channel, and an outlet for removing reagent(s) from the flow channel. In some examples, the flow cell enables the detection of the reaction that occurs in the chamber. For example, the flow cell may include one or more transparent surfaces allowing for the optical detection of arrays, optically labeled molecules, or the like within the flow channel.

As used herein, a "flow channel" or "channel" may be an area defined between two bonded components, which can selectively receive a liquid sample. In some examples, the flow channel may be defined between a patterned substrate and a lid, and thus may be in fluid communication with one or more depressions defined in the patterned substrate or, for example, a patterend resin of the patterned substrate. The flow channel may also be defined between two patterned substrate surfaces that are bonded together.

A "functional group pair" refers to two functional groups that are different in structure and in their chemical functionality. The different functionalities enable the pair to respectively attach to different silanes and/or to different primer sets (e.g., primer sets with different terminal groups). The different functional groups may be considered a pair, in part because they enable the orthogonal polymers to be simultaneously applied.

As used herein, "heteroalicyclic" or "heteroalicycle" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heteroalicyclic ring system may optionally contain one or more unsaturated bonds situated in such a way, however, that a fully delocalized pi-electron system does not occur throughout all the rings. The heteroatoms are independently selected from oxygen, sulfur, and nitrogen. A heteroalicyclic ring system may further contain one or more carbonyl or thiocarbonyl functionalities, so as to make the definition include oxo-systems and thio-systems such as lactams, lactones, cyclic imides, cyclic thioimides, and cyclic carbamates. The rings may be joined together in a fused fashion. Additionally, any nitrogens in a heteroalicyclic may be quaternized. Heteroalicycle or heteroalicyclic groups may be unsubstituted or substituted. Examples of such "heteroalicyclic" or "heteroalicycle" groups include 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

A "(heteroalicyclic)alkyl" refers to a heterocyclic or a heteroalicyclic group connected, as a substituent, via a lower alkylene group. The lower alkylene and heterocycle or a heterocycle of a (heteroalicyclic)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

As used herein, "hydroxy" or "hydroxyl" refers to an —OH group.

The term "glycol" refers to the end group —$(CH_2)_n$OH, where n ranges from 2 to 10. As specific examples, the glycol may be an ethylene glycol end group —$CH_2CH_2$OH, a propylene glycol end group —$CH_2CH_2CH_2$OH, or a butylene glycol end group —$CH_2CH_2CH_2CH_2$OH.

As used herein, the term "interstitial region" refers to an area, e.g., of a patterned substrate, patterned resin, or other support that separates depressions. For example, an interstitial region can separate one depression of an array from another depression of the array. The two depressions that are separated from each other can be discrete, i.e., lacking physical contact with each other. In many examples, the interstitial region is continuous whereas the depressions are discrete, for example, as is the case for a plurality of depressions defined in an otherwise continuous surface. In other examples, the interstitial regions and the features are discrete, for example, as is the case for a plurality of trenches separated by respective interstitial regions. The separation provided by an interstitial region can be partial or full separation. Interstitial regions may have a surface material that differs from the surface material of the depressions defined in the surface. For example, depressions can have orthogonal polymers and two different primers set therein, and the interstitial regions can be free of orthogonal polymers and primer sets.

As used herein, a "negative photoresist" refers to a light-sensitive material in which a portion that is exposed to light of particular wavelength(s) becomes insoluble to a developer. In these examples, the insoluble negative photoresist has less than 5% solubility in the developer. With the negative photoresist, the light exposure changes the chemical structure so that the exposed portions of the material becomes less soluble (than non-exposed portions) in the developer. While not soluble in the developer, the insoluble negative photoresist may be at least 99% soluble in a remover that is different from the developer. The remover may be a solvent or solvent mixture used, e.g., in a lift-off process.

In contrast to the insoluble negative photoresist, any portion of the negative photoresist that is not exposed to light is at least 95% soluble in the developer. In some examples, the portion of the negative photoresist not exposed to light is at least 98%, e.g., 99%, 99.5%, 100%, soluble in the developer.

As used herein, a "nucleotide" includes a nitrogen containing heterocyclic base, a sugar, and one or more phosphate groups. Nucleotides are monomeric units of a nucleic acid sequence. In ribonucleic acids (RNA), the sugar is a ribose, and in deoxyribonucleic acids (DNA), the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

A "patterned resin" refers to any polymer that can have depressions defined therein. Specific examples of resins and techniques for patterning the resins will be described further herein.

The term "polymer" refers to a homopolymer, a copolymer, or a terpolymer. In some examples, the polymer is a linear polymer and in other examples, the polymer is a multi-arm polymer. A linear polymer is a chain in which all of the carbon-carbon bonds exist in a single straight line. A multi-arm polymer includes a central molecule/compound that has arms/branches extending therefrom. A 2-arm multi-arm polymer is also linear. As mentioned above, "orthogonal" refers to two different polymers, each of which has different functional groups for attachment to the substrate and for attachment to a different primer set.

As used herein, a "positive photoresist" refers to a light-sensitive material in which a portion that is exposed to light of particular wavelength(s) becomes soluble to a developer. In these examples, any portion of the positive photoresist exposed to light is at least 95% soluble in the developer. In some examples, the portion of the positive photoresist exposed to light is at least 98%, e.g., 99%, 99.5%, 100%, soluble in the developer. With the positive photoresist, the light exposure changes the chemical structure so that the exposed portions of the material become more soluble (than non-exposed portions) in the developer.

In contrast to the soluble positive photoresist, any portion of the positive photoresist not exposed to light is insoluble (less than 5% soluble) in the developer. While not soluble in the developer, the insoluble positive photoresist may be at least 99% soluble in a remover that is different from the developer. In some examples, insoluble positive photoresist is at least 98%, e.g., 99%, 99.5%, 100%, soluble in the remover. The remover may be a solvent or solvent mixture used in a lift-off process.

As used herein, the term "primer" is defined as a single stranded nucleic acid sequence (e.g., single strand DNA). Some primers are part of a primer set, which serve as a starting point for template amplification and cluster generation. Other primers, referred to herein as sequencing primers, serve as a starting point for DNA synthesis. The 5' terminus of a primer set may be modified to allow a coupling reaction with a functional group of one of the orthogonal polymers. The primer length can be any number of bases long and can include a variety of non-natural nucleotides. In an example, the sequencing primer is a short strand, ranging from 10 to 60 bases, or from 20 to 40 bases.

The term "primer set" refers to a pair of primers that together enable the amplification of a template nucleic acid strand. Opposed ends of the template strand include adapters to hybridize to the respective primers in a set.

The term "substrate" refers to a structure upon which various components of the flow cell (e.g., the orthogonal polymers, primer(s), etc.) may be added. The substrate may be a wafer, a panel, a rectangular sheet, a die, or any other suitable configuration. The substrate is generally rigid and is insoluble in an aqueous liquid. The substrate may be inert to the chemistry that is present in the depressions. For example, a substrate can be inert to chemistry used to attach the primer(s), used in sequencing reactions, etc. The substrate may be a single layer structure, or a multi-layered structure (e.g., including a support and a patterned resin on the support). Examples of suitable substrates will be described further herein.

As used herein, the terms "tetrazine" and "tetrazinyl" refer to six-membered heteroaryl group comprising four nitrogen atoms. Tetrazine can be optionally substituted.

Orthogonal Polymers

In the examples disclosed herein, two polymers are used together on a flow cell substrate, and these polymers are orthogonal. These orthogonal polymers are referred to herein as the first polymer and the second polymer. The first and second polymers are orthogonal in that that they include respective functional groups that can attach to two different silanes on the substrate surface. The first and second polymers are also orthogonal in that they include respective functional groups that can attach to different primer sets. In some instances, each polymer has a different type of functional group that is capable of both silane attachment and primer set attachment. In other instances, each polymer has at least two different types of functional groups, one of which is capable of silane attachment and another of which is capable of primer set attachment.

Generally, the first and second polymers respectively include a first functional group and a second functional group of a functional group pair. As such, first functional group is part of the first polymer and the second functional group is part of the second polymer. As examples, the functional group pair is selected from the group consisting of an activated ester functional group and an azide functional group, a tetrazine functional group and an activated ester functional group, and a tetrazine functional group and an azide functional group. In addition to the respective functional groups of the pair, one or both of the first and second polymers may have additional functional groups. These additional functional groups may be selected to introduce additional functionality into the polymers. For example, one of the functional groups can react with the silane and one or more other functional groups can graft the primer set.

Each of the orthogonal polymers set forth herein may be synthesized using reversible addition-fragmentation chain transfer (RAFT) polymerization. While RAFT polymerization may be used, it is to be understood that other polymerization processes may also be used. Other suitable polymerization processes include atom transfer radical polymerization (ATRP), nitroxide mediated radical (NMP) polymerization in combination with RAFT or ATRP, NMP with an additional cross-linking step, cobalt-mediated polymerization, group transfer polymerization (GTP), ring opening polymerization (ROP), ionic polymerization, or any other polymerization process that either directly or indirectly yields the desired linear or multi-arm architecture.

Any of these polymerization processes may be used to generate a linear polymer or a multi-arm polymer, where the desired monomer(s) are incorporated, respectively, along the linear chain or into each arm. It is to be understood that a 2-arm polymer is linear, except that it has a central molecule from which the 2-arms extend. This is unlike other linear polymers, which have repeating monomer units and no central molecule. When copolymers or terpolymers are synthesized, the monomers may be incorporated statistically, randomly, alternatingly, or in block along the chain or in the arms depending upon the polymerization process that is used.

RAFT polymerization of one or more monomers is initiated with a reversible addition-fragmentation chain transfer agent (a RAFT agent, examples of which are provided herein). The monomer or monomers used will depend upon the polymer (e.g., homopolymer, copolymer, terpolymer, etc.) that is to be synthesized, and whether the desired functional group is to be incorporated during polymerization or post-polymerization.

In some examples, each of the first and second polymers is a different homopolymer. By "homopolymer," it is meant that a single monomer is used in the desired polymerization process. The resulting polymer may be a linear polymer or a multi-arm polymer. In other examples, each of the first and second polymers is a different copolymer. By "copolymer," it is meant that two different monomers are used in the desired polymerization process. The resulting copolymer may be a linear copolymer or a multi-arm copolymer. In still other examples, each of the first and second polymers is a different terpolymer. By "terpolymer," it is meant that three different monomers are used in the desired polymerization process. The resulting terpolymer may be a linear copolymer or a multi-arm copolymer.

Orthogonal Polymers—Activated Ester and Azide Functional Group Pairs

In one example, the first polymer is a first homopolymer and the first functional group is the activated ester functional group, and the second polymer is a second homopolymer and the second functional group is the azide functional group. In this example, the first homopolymer may be polymerized from a monomer that includes the activated ester functional group and the second homopolymer may be polymerized from a monomer that includes the azide functional group.

In this example, the activated ester functional group (of the first orthogonal polymer) is capable of binding to a silane that includes an amine functional group, and is also capable of binding to an amine-terminated primer. Any monomer that can be polymerized via the desired polymerization process and that includes this type of activated ester functional group may be used. The azide functional group (of the second orthogonal polymer) is either i) capable of binding to a silane that includes an alkyne functional group and is also capable of binding to an alkyne-terminated primer or ii) capable of binding to a silane that includes a norbornene functional group and is also capable of binding to an alkyne-terminated primer. Any monomer that can be polymerized via the desired polymerization process and that includes this type of azide functional group may be used.

The synthesis of this example of the first polymer involves polymerization of a first monomer including the activated ester functional group, and the first monomer is selected from the group consisting of pentafluorophenyl acrylate:

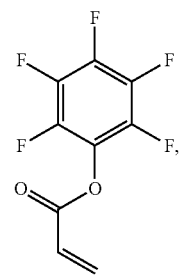 [SMILES: C=CC(=O)Oc1c(F)c(F)c(F)c(F)c1F]

pentafluorophenyl methacrylate:

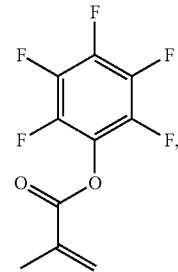 [SMILES: C=C(C)C(=O)Oc1c(F)c(F)c(F)c(F)c1F]

and vinyl dimethyl azlactone

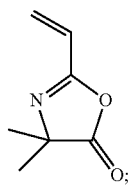

and the synthesis of this example of the second polymer involves polymerization of a second monomer including the azide functional group, and the second monomer has structure I:

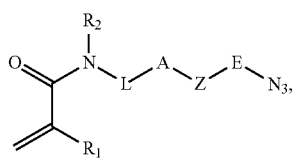

wherein $R_1$ is hydrogen or an alkyl; $R_2$ is hydrogen or an alkyl; L is a linker including a linear chain of 2 atoms to 20 atoms selected from the group consisting of carbon, oxygen, and nitrogen and optional substituents on the carbon and any nitrogen atoms in the chain; A is an N substituted amide having structure II:

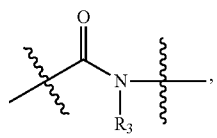

where $R_3$ is hydrogen or an alkyl; E is a linear chain of 1 atom to 4 atoms selected from the group consisting of carbon, oxygen and nitrogen, and optional substituents on the carbon and any nitrogen atoms in the chain; and Z is an optional nitrogen containing heterocycle.

As noted above, $R_1$ and $R_2$ may both be hydrogen atoms. However, when $R_1$ and/or $R_2$ in structure I is an alkyl, the number of carbons may range from 1 to 6 or from 1 to 4.

Also in structure I, E may be an optionally substituted C1-C4 alkylene, where each carbon is optionally substituted with one or more substituents selected from, for example, C1-C4 alkyl, —OH, —OC1-C4 alkyl, or =O. As examples, E may be an unsubstituted C1-C4 alkylene, for example $CH_2$, $(CH_2)_2$, $(CH_2)_3$ or $(CH_2)_4$. In other examples, E may include an ether, an ester or an amide. For example, E may include —$CH_2CH_2OCH_2$—, —COCNHCH$_2$— or —$CH_2COOCH_2$—.

Also in structure I, L may be a linker including a linear chain that is a —C2-C20 alkylene- or a 3 to 20 atom linear heteroalkylene, each of which may be optionally substituted with one or more substituents selected from the group consisting of —C1-C4 alkyl, —OH, —OC1-C4 alkyl, or =O. L may be a linker with a linear chain that is a —C2-C6 alkylene-, optionally substituted with one or more —C1-C4 alkyl, —OH, —OC1-C4 alkyl, or =O substituents. L may be unsubstituted —C2-C6 alkylene- (also drawn as —$(CH_2)_{2-6}$—), for example L may be unsubstituted —C3-C4 alkylene-, for example —$(CH_2)_3$— or —$(CH_2)_4$—. In other examples, L may be a linker including a linear chain that is a 3 to 20 atom linear heteroalkylene, which may be optionally substituted with one or more substituents selected from the group consisting of —C1-C4 alkyl, —OH, —OC1-C4 alkyl, or =O. L may include one or more ethylene glycol units. L may be —$CH_2CH_2(OCH_2CH_2)_x$—$OCH_2CH_2$—, in which x is 0 to 10. In one example, x is 1, 2, 3, 4, 5, or 6. L may include one or more amide groups. For example, L may be —C2-C6 alkyl-NHC(O)—C2-C6 alkyl-, or L may be —$(CH_2)_2$—NHC(O)—$(CH_2)_2$— or —$(CH_2)_3$—NHC(O)—$(CH_2)_2$—. L may include one or more natural or unnatural amino acids, for example L may include one or more amino acids selected from the group consisting of glycine, alanine, valine, isoleucine, leucine, lysine, serine, threonine, cysteine, asparagine, or glutamine. In some examples, L may comprise 1, 2, or 3 amino acid units.

Also in structure I, the N substituted amide, A, may be bonded to L and Z in two possible configurations, for example the carbonyl carbon of A may be bonded to L and the amide nitrogen of A may be bonded to Z. Alternatively, the carbonyl carbon of A may be bonded to Z and the amide nitrogen of A may be bonded to L.

Also in structure I, Z may include a nitrogen containing heterocycle having from 5 to 10 ring members (from 5 to 10 atoms), e.g., a 5 to 10 membered heterocyclic ring, wherein the ring members are the atoms that form the back bone of the heterocyclic ring. Z may include a single cyclic structure or a fused structure comprising two or more ring systems. In the case of single cyclic structure, Z may comprise 5 or 6 ring members, e.g., Z may be a 5 or 6 membered heterocyclic ring. In the case of fused structure, Z may include 9 or 10 ring members. The nitrogen containing heterocycle may include more than one heteroatom, for example one or more additional nitrogen heteroatoms, or one or more oxygen heteroatoms, or one or more sulphur heteroatoms, or any suitable combination of such heteroatoms. The nitrogen containing heterocycle may be aromatic, for example pyridinyl, pyrimidinyl, pyrrolyl, pyrrazolyl, imidazolyl, indolyl, quinolinyl, quinazolinyl. The nitrogen containing heterocycle may be aliphatic, for example a cycloalkyl. The aliphatic nitrogen containing heterocycle may be saturated or may include one or more double bonds while not being aromatic. In one example, the aliphatic nitrogen containing heterocycle may be pyrrolidinyl, pyridinyl, or pyrimidinyl.

One specific example of the monomer including the azide functional group (which does not include Z) is azido acetamido pentyl acrylamide, and specifically N-(5-azidoacetamidylpentyl) acrylamide. Variations of N-(5-azidoacetamidylpentyl) acrylamide may also be used, for example, the alkyl chain —$(CH_2)$— may range from 1 to 20 and/or each of the —$(CH_2)$— can be optionally substituted. Some other examples of the monomer including the azide functional group (which do include Z) are:

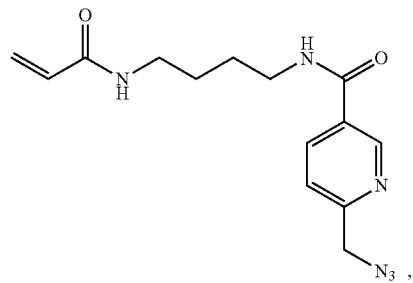

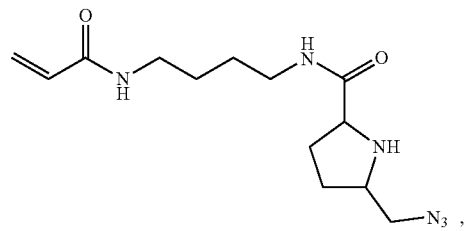

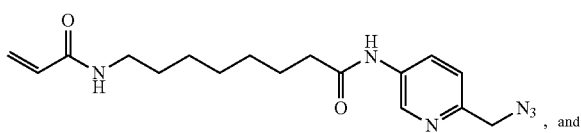

and

-continued

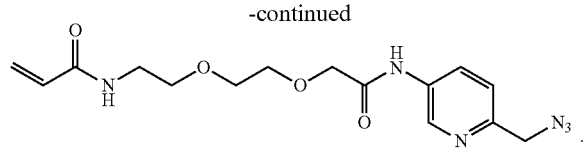

An example of the first homopolymer including a plurality of the activated ester functional groups is shown below:

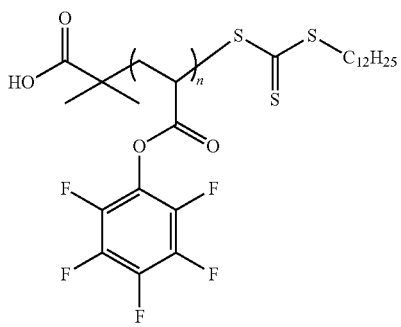

In this example, the first monomer is pentafluorophenyl acrylate and n is an integer in the range of 1 to 50,000. An example of the second homopolymer including a plurality of the azide functional groups is shown below:

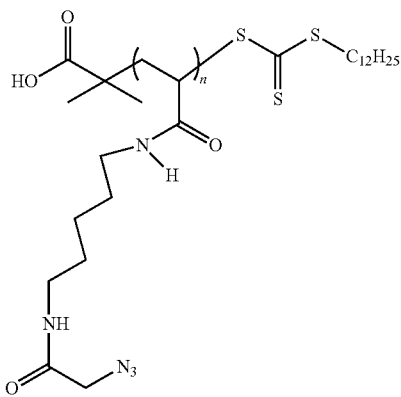

In this example, the second monomer is N-(5-azidoacetamidylpentyl) acrylamide and n is an integer in the range of 1 to 50,000.

These example homopolymers are linear polymers that are generated with 2-(dodecylthiocarbonothioylthio)-2-methylpropionic acid as the RAFT agent (discussed below). Another example of the RAFT agent may be used with the activated ester functional group monomers or the azide functional group monomers in order to form different examples of the linear homopolymers. Alternatively, a dendritic RAFT agent may be used with the activated ester functional group monomers or the azide functional group monomers in order to form different examples of the multi-arm homopolymers. Any of the multi-arm homopolymers will include the polymerized monomer in each of the arms. In any of these examples, the RAFT agent end groups may be cleaved and replaced with other end groups, such as a hydroxyl, a substituted amide, etc. Moreover, any of the other polymerization processes described herein may be used to generate the homopolymers.

The synthesis of the polymer with the azide functional group may alternatively involve polymerization of a first monomer including a functional group that can be substituted with the azide functional group post polymerization. In one example, a halogenated monomer (e.g., structure I where $N_3$ is replaced with a halogen, such as bromine, chloride, fluorine, or iodine) may be used, as the polymer can be reacted with $NaN_3$ to replace the halogen in the polymer with the azide. As such, in one example, the synthesis of the polymer with the azide functional group involves polymerizing a first monomer including a halogen functional group, and replacing the halogen functional group with the azide functional group.

Other examples of the first and second orthogonal polymers that can be synthesized, respectively, with the monomer containing the activated ester functional group and the monomer containing the azide functional group, may be copolymers.

To generate one example of these first and second orthogonal copolymers, the synthesis of the first copolymer involves polymerization of the first monomer including the activated ester functional group and a first acrylamide monomer having structure III:

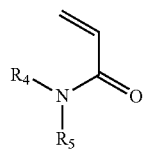

wherein $R_4$ and $R_5$ are independently selected from the group consisting of an alkyl, an alkylamino, an alkylamido, an alkylthio, an aryl, a glycol, and optionally substituted variants thereof; and the synthesis of the second copolymer involves polymerization of the second monomer including the azide functional group and a second acrylamide monomer having structure III':

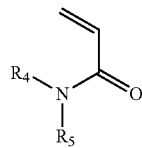

wherein $R_4$ and $R_5$ are independently selected from the group consisting of an alkyl, an alkylamino, an alkylamido, an alkylthio, an aryl, a glycol, and optionally substituted variants thereof. As depicted, structures III and III' are the same. In an example when the first orthogonal copolymer, including the activated ester functional group and the first acrylamide monomer, and the second orthogonal copolymer, including the azide functional group and the second acrylamide monomer, are utilized, it is to be understood that the first and second acrylamide monomers may be the same or different.

With these specific examples of the first and second orthogonal copolymers, the activated ester functional group (of the first orthogonal copolymer) is capable of binding to a silane that includes an amine functional group and is also capable of binding to an amine-terminated primer. The azide functional group (of the second orthogonal copolymer) is capable of binding to a silane that includes a norbornene functional group and is also capable of binding to an alkyne-terminated primer.

An example of the first copolymer is shown below:

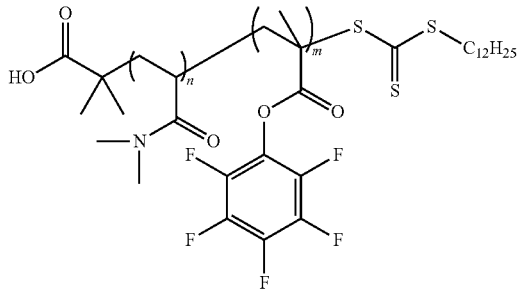

In this example, the first monomer is pentafluorophenyl methacrylate, the first acrylamide monomer is dimethylacrylamide, n is an integer in the range of 1 to 50,000 (e.g., from about 1 to 5,000), and m is an integer in the range of 1 to 100,000 (e.g., 1 to 10,000). An example of the second copolymer is shown below:

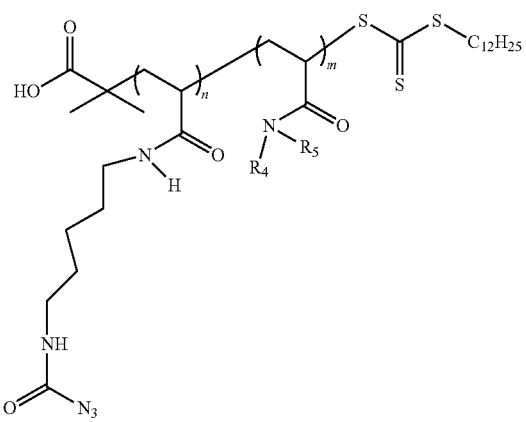

In this example, the second monomer is N-(5-azidoacetamidylpentyl) acrylamide, the first acrylamide monomer is acrylamide, n is an integer in the range of 1 to 50,000 (e.g., from 1 to 5,000), and m is an integer in the range of 1 to 100,000 (e.g., from 1 to 10,000).

These example copolymers are linear polymers that are generated with 2-(dodecylthiocarbonothioylthio)-2-methylpropionic acid as the RAFT agent. Another example of the RAFT agent may be used with the activated ester functional group monomers or the azide functional group monomers in order to form different examples of the linear copolymers. Alternatively, a dendritic RAFT agent may be used with the activated ester functional group monomers or the azide functional group monomers in order to form different examples of the multi-arm copolymers. Any of the multi-arm copolymers will include the polymerized monomers in each of the arms. In any of these examples, the RAFT agent end groups may be cleaved and replaced with other end groups, such as a hydroxyl, a substituted amide, etc. Moreover, any of the other polymerization processes described herein may be used to generate the homopolymers.

In any of the examples disclosed herein, the examples set forth for the first polymer may be used as the second polymer and the examples set forth for the second polymer may be used as the first polymer, as long as the polymers used together on the flow cell surface are orthogonal and include an example of the functional group pair defined herein. For example, the first polymer may be a copolymer synthesized with the monomer including the azide functional group and an acrylamide monomer; and the second polymer may be a copolymer synthesized with the monomer including the activated ester functional group and another acrylamide monomer. In this example of the first copolymer, the first functional group is the azide functional group and the first copolymer further includes an additional functional group that includes an acrylamide; and in this example of the second copolymer, the second functional group is the activated ester functional group and the second copolymer further includes an additional functional group that includes an acrylamide.

Orthogonal Polymers—Tetrazine and Activated Ester Functional Group Pairs

The first and second polymers of a set of orthogonal polymers may be polymers that respectively include a tetrazine functional group and an activated ester functional group (one example of a functional group pair as defined herein).

In one example, the first polymer is a first homopolymer and the first functional group is the tetrazine functional group, and the second polymer is a second homopolymer and the second functional group is the activated ester functional group. In this example, the first homopolymer may be polymerized from a monomer that includes the tetrazine functional group and the second homopolymer may be polymerized from a monomer that includes the activated ester functional group. Alternatively, the first homopolymer may be polymerized from a monomer that does not include the tetrazine functional group, and the tetrazine functional group may be introduced to the homopolymer post polymerization.

In this example, the tetrazine functional group (of the first orthogonal polymer) is capable of binding to a silane that includes a norbornene functional group and is also capable of binding to a bicyclo[6.1.0]nonyne (BCN)-terminated primer or a norbornene-terminated primer. Any monomer that can be polymerized via the desired polymerization process and that includes this type of tetrazine functional group may be used. Also in this example, the activated ester functional group is capable of binding to a silane that includes an amine functional group and is also capable of binding to an amine-terminated primer. Any of the monomers described herein that include the activated ester functional group may be used.

In one example, the synthesis of this example of the first homopolymer involves polymerization of a first monomer including the tetrazine functional group, where the first monomer is selected from the group consisting of structure IV:

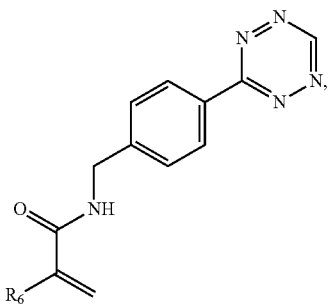

wherein $R_6$ is H or a methyl, and structure V:

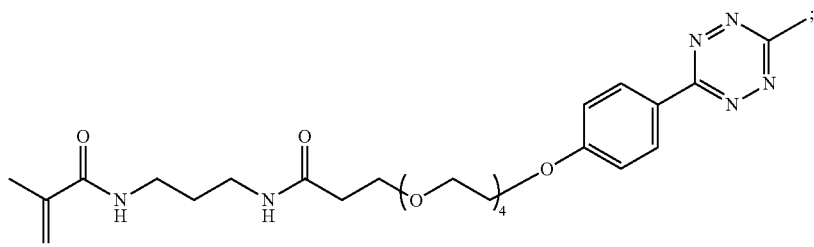

and the synthesis of the second homopolymer involves polymerization of a second monomer including the activated ester functional group, wherein the second monomer is selected from the group consisting of pentafluorophenyl acrylate, pentafluorophenyl methacrylate, and vinyl dimethyl azlactone.

In another example, the synthesis of this example of the polymer with the tetrazine functional group involves polymerization of a first monomer including a functional group that can be substituted with the tetrazine functional group post polymerization. In one example, an activated ester monomer may be used, as its polymer is soluble in a wide range of solvents and can be substituted easily with amines (e.g., tetrazine amine), alcohols (e.g., tetrazine-PEG3-alcohol), or thiols (e.g., thiol-PEG-tetrazine) at different molar equivalence. In another example, N-(3-aminopropyl)methacrylamide hydrochloride may be used, as the amine can be easily reacted with any tetrazine terminated with an N-Hydroxysuccinimide (NHS) ester, such as tetrazine-PEG4-NHS ester, tetrazine-PEG5-NHS ester, etc. As such, in one example, the synthesis of the polymer with the tetrazine functional group involves polymerizing a first monomer including an activated ester or an amine functional group, and replacing the activated ester or the amine functional group with the tetrazine functional group.

Other examples of the first and second orthogonal polymers that can be synthesized, respectively, with the monomer containing the tetrazine functional group and the monomer containing the activated ester functional group, may be copolymers.

To generate one example of these first and second orthogonal copolymers, the synthesis of the first copolymer involves polymerization of the first monomer including the tetrazine functional group and a first additional monomer having structure I (with the azide functional group as described herein); and the synthesis of the second polymer involves polymerization of the second monomer including the activated ester functional group and a second additional monomer, the second additional monomer including an aryl-iodide. Any aryl-iodide monomer may be used, including iodobenzene, iodobenzene substituted with an aryl or an alkenyl group, or the like.

With these specific examples of the first and second orthogonal copolymers, the tetrazine functional group (of the first orthogonal copolymer) is capable of binding to a silane that includes a norbornene functional group and the azide functional group is capable of binding to an alkyne-terminated primer. The activated ester functional group (of the second orthogonal copolymer) is capable of binding to a silane that includes an amine functional group and the aryl-iodide functional group is capable of binding to a boronic acid-terminated primer.

Still other examples of the first and second orthogonal polymers that can be synthesized, respectively, with the monomer containing the tetrazine functional group and the monomer containing the activated ester functional group, may be terpolymers.

In one example, the first polymer is a first terpolymer, where the first functional group is the tetrazine functional group and the first terpolymer further includes two additional functional groups that include an azide and an acrylamide; and the second polymer is a second terpolymer, where the second functional group is the activated ester functional group and the second terpolymer includes two additional functional groups that include an aryl-iodide and an acrylamide. To generate these examples of these first and second orthogonal terpolymers, the synthesis of the first terpolymer involves polymerization of the first monomer including the tetrazine functional group, a first additional monomer, and a second additional monomer, the first additional monomer having structure I (with the azide functional group as described herein), and the second additional monomer having structure III (the acrylamide monomer as described herein); and the synthesis of the second polymer involves polymerization of the second monomer including the activated ester functional group, a third additional monomer, and a fourth additional monomer, the third additional monomer including an aryl-iodide, and the fourth additional monomer having structure III' (the acrylamide monomer as described herein). In an example when the first orthogonal terpolymer (including the tetrazine, the azide and the acrylamide functional groups) and the second terpolymer (including the activated ester, aryl-iodide and acrylamide functional groups) are utilized, it is to be understood that the second additional monomer (structure III) and the fourth additional monomer (structure III') may be the same or different.

With these specific examples of the first and second orthogonal terpolymers, the tetrazine functional group (of the first orthogonal terpolymer) is capable of binding to a silane that includes a norbornene functional group and the azide functional group is capable of binding to an alkyne-terminated primer. The activated ester functional group (of the second orthogonal terpolymer) is capable of binding to a silane that includes an amine functional group and the aryl-iodide functional group is capable of binding to a boronic acid-terminated primer.

Any of the agents (e.g., RAFT agents) or dendritic agents (e.g., dendritic RAFT agents) may be used to generate linear polymers or multi-arm polymers including the tetrazine and activated ester functional group pair.

Moreover, in any of the examples disclosed herein, the examples set forth for the first polymer may be used as the second polymer and the examples set forth for the second polymer may be used as the first polymer, as long as the polymers used together on the flow cell surface are orthogonal and include an example of the functional group pair defined herein. For example, the first polymer may be a copolymer synthesized with the monomer including the activated ester functional group and a monomer including the aryl-iodide functional group; and the second polymer may be a copolymer synthesized with the monomer including the tetrazine functional group and a monomer including the azide functional group.

Orthogonal Polymers—Tetrazine and Azide Functional Group Pairs

The first and second polymers of a set of orthogonal polymers may be polymers that respectively include a tetrazine functional group and an azide functional group (one example of a functional group pair as defined herein).

In one example, the first polymer is a first homopolymer and the first functional group is the tetrazine functional group, and the second polymer is a second homopolymer and the second functional group is the azide functional group. In this example, the first homopolymer may be polymerized from a monomer that includes the tetrazine functional group and the second homopolymer may be polymerized from a monomer that includes the azide functional group. Alternatively, the first homopolymer may be polymerized from a monomer that does not include the tetrazine functional group, and the tetrazine functional group may be introduced to the homopolymer post polymerization.

In this example, the tetrazine functional group (of the first orthogonal polymer) is capable of binding to a silane that includes a norbornene functional group and is also capable of binding to a norbornene-terminated primer. Any monomer that can be polymerized via the desired polymerization process and that includes this type of tetrazine functional group may be used. The azide functional group (of the second orthogonal polymer) is capable of binding to a silane that includes an alkyne functional group and is also capable of binding to an alkyne-terminated primer. Any monomer that can be polymerized via the desired polymerization process and that includes this type of azide functional group may be used.

In one example, the synthesis of this example of the first homopolymer involves polymerization of a first monomer including the tetrazine functional group, where the first monomer is selected from the group consisting of structure IV (with the tetrazine functional group as described herein) and structure V (with the tetrazine functional group as described herein); and the synthesis of the second homopolymer involves polymerization of a second monomer including the azide functional group, and the second monomer having structure I (with the azide functional group as described herein).

In another example, the synthesis of this example of the homopolymer with the tetrazine functional group involves polymerization of a first monomer including a functional group that can be substituted with the tetrazine functional group post polymerization. In one example, an activated ester monomer may be used, as its polymer is soluble in a wide range of solvents and can be substituted easily with amines (e.g., tetrazine amine), alcohols (e.g., tetrazine-PEG3-alcohol), or thiols (e.g., thiol-PEG-tetrazine) at different molar equivalence. In another example, N-(3-aminopropyl)methacrylamide hydrochloride may be used, as the amine can be easily reacting with any tetrazine terminated with an N-Hydroxysuccinimide (NHS) ester, such as tetrazine-PEG4-NHS ester, tetrazine-PEG5-NHS ester, etc. As such, in one example, the synthesis of the polymer with the tetrazine functional group involves polymerizing a first monomer including an activated ester or an amine functional group, and replacing the activated ester or the amine functional group with the tetrazine functional group.

In another example, the synthesis of this example of the homopolymer with the azide functional group involves polymerization of a first monomer including a functional group that can be substituted with the azide functional group post polymerization. In one example, a halogenated monomer may be used, as the halogens in its polymer can be substituted easily with the azides.

Any of the agents or dendritic agents may be used to generate linear polymers or multi-arm polymers including the tetrazine and azide functional group pair.

Moreover, in any of the examples disclosed herein, the examples set forth for the first polymer may be used as the second polymer and the examples set forth for the second polymer may be used as the first polymer, as long as the polymers used together on the flow cell surface are orthogonal and include an example of the functional group pair defined herein. For example, the first polymer may be a homopolymer synthesized with the monomer including the azide functional group; and the second polymer may be a homopolymer synthesized with the monomer including the tetrazine functional group.

In any of the examples set forth herein, the resulting polymer may have a weight average molecular weight ranging from about 10,000 g/mol to about 2,000,000 g/mol. For simultaneous paired end read applications, the polymer may have a lower weight average molecular weight ranging from about 10,000 g/mol to about 75,000 g/mol. In other examples, the polymer may have a weight average molecular weight ranging from about 1,000,000 to about 2,000,000.

Polymer Synthesis

Any suitable polymerization technique may be used to generate any of the polymers set forth herein.

For example, any of the polymers set forth herein may be generated using RAFT polymerization. As mentioned, RAFT polymerization of the monomer(s) for any example of the polymers disclosed herein is initiated with a RAFT agent. The RAFT agent selected dictates the polymer structure that will be formed (e.g., a linear chain, a multi-arm structure).

Each RAFT agent includes the thiocarbonylthio group (S═C—S) with substituents R and Z that impact the polymerization reaction kinetics and the degree of structural control. As examples, the thiocarbonylthio group may be selected from the group consisting of a dithiobenzoate:

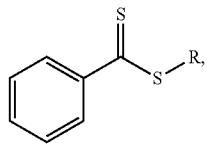

a trithiocarbonate:

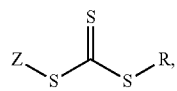

and a dithiocarbamate:

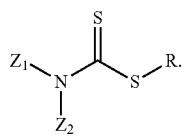

The R-group in the RAFT agent is a free radical leaving group, and the Z-group(s) control C═S bond reactivity and influence the rate of radical addition and fragmentation.

Some examples of suitable RAFT agents for (meth) acrylate or (meth)acrylamide monomer polymerization include 2-(dodecylthiocarbonothioylthio)-2-methylpropionic acid, 4-cyano-4-[(dodecylsulfanylthiocarbonyl)sulfanyl]pentanoic acid, 2-cyano-2-propyl dodecyl trithiocarbonate, and 4-cyano-4-(phenylcarbonothioylthio)pentanoic acid. 2-cyanomethyl dodecyl trithiocarbonate is a suitable RAFT agent for acrylate and acrylamide monomers. 2-cyano-2-propyl benzodithioate is a suitable RAFT agent for (meth)acrylate and methacrylamide monomer polymerization. In one example, the RAFT agent is 4-cyano-4-[(dodecylsulfanylthiocarbonyl)sulfanyl]pentanoic acid. Any of these RAFT agents may be used to generate linear polymers.

A dendritic RAFT agent may be used to generate multi-arm polymers. The dendritic RAFT agent includes a central molecule/compound and arms (or branches) that extend from the central molecule/compound. The dendritic RAFT agent may have from 2 arms to 30 arms, each of which includes the thiocarbonylthio groups at or near the end of each arm, or alternatively, near the central molecule/compound.

The central molecule/compound of the dendritic RAFT agent may be any multi-functional molecule, such as macrocycles (e.g., cyclodextrins, porphyrins, etc.), extended pi-systems (e.g., perylenes, fullerenes, etc.), metal-ligand complexes, polymeric cores, etc. Some specific examples of the central molecule/compound of the dendritic RAFT agent include a phenyl group, benzoic acid, pentaerythritol, a phosphazene group, etc.

Any of the RAFT agents set forth herein may be contained within each arm of a dendritic RAFT agent.

In some examples, the dendritic RAFT agent has an R-group configuration, where the central molecule is the leaving group during the chain transfer process. Two examples of the dendritic RAFT agent having the R-group RAFT agent configuration are:

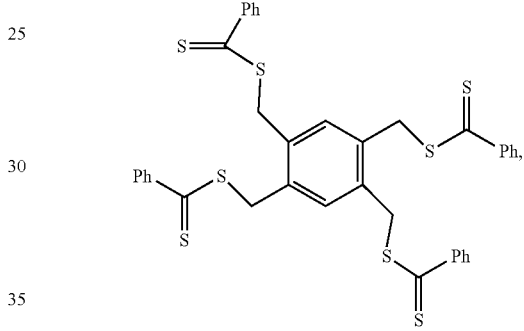

where Ph is a phenyl group, and

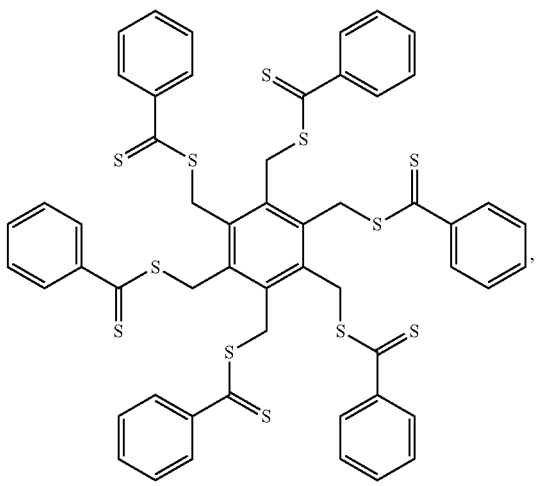 [SMILES: S=C(SCc1c(CSC(=S)c2ccccc2)c(CSC(=S)c2ccccc2)c(CSC(=S)c2ccccc2)c(CSC(=S)c2ccccc2)c1CSC(=S)c1ccccc1)c1ccccc1]

In other examples, the dendritic RAFT agent has a Z-group configuration. In these examples, the reactive polymeric arms are detached from the central molecule/compound during growth, and to undergo chain transfer, again react at the central molecule/compound. One example of the dendritic RAFT agent having a Z-group RAFT configuration is:

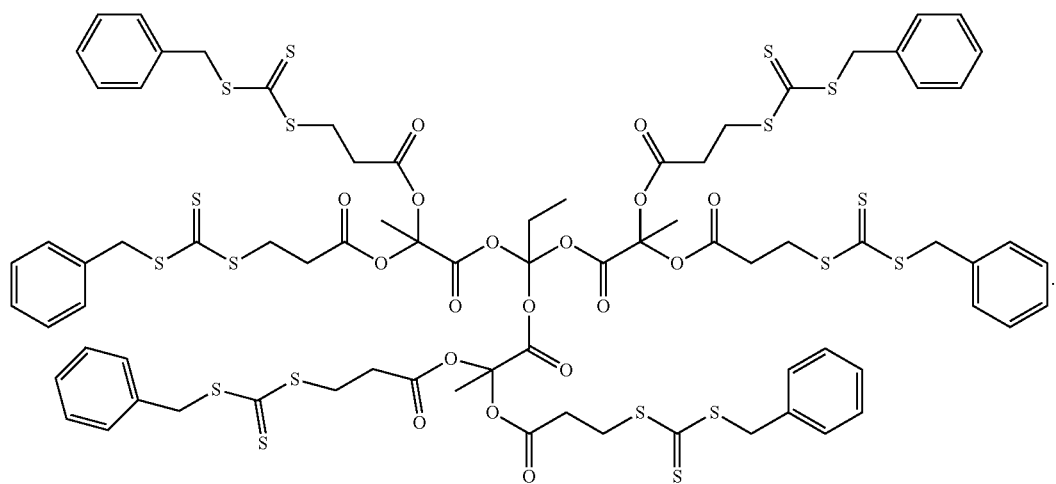 [SMILES: CCC(OC(=O)C(C)(OC(=O)CCSC(=S)SCc1ccccc1)OC(=O)CCSC(=S)SCc1ccccc1)(OC(=O)C(C)(OC(=O)CCSC(=S)SCc1ccccc1)OC(=O)CCSC(=S)SCc1ccccc1)OC(=O)C(C)(OC(=O)CCSC(=S)SCc1ccccc1)OC(=O)CCSC(=S)SCc1ccccc1]
In an example, the dendritic RAFT agent is selected from the group consisting of 3,5-Bis(2-dodecylthiocarbonothioylthio-1-oxopropoxy)benzoic acid:
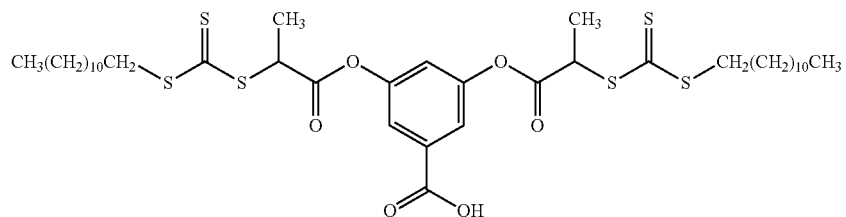
(an example of a 2-arm dendritic RAFT agent); 1,1,1-Tris[(dodecylthiocarbonothioylthio)-2-methylpropionate]ethane:
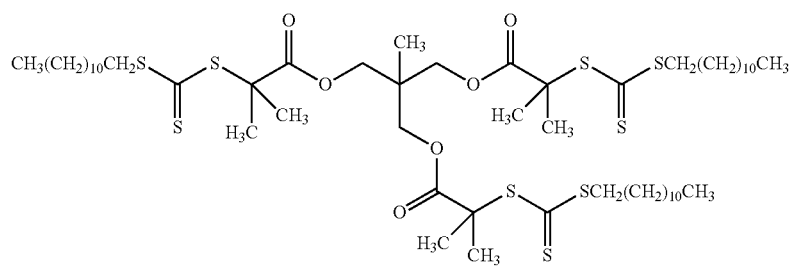

(an example of a 3-arm dendritic RAFT agent); and Pentaerythritol tetrakis[2-(dodecylthiocarbonothioylthio)-2-methylpropionate]:

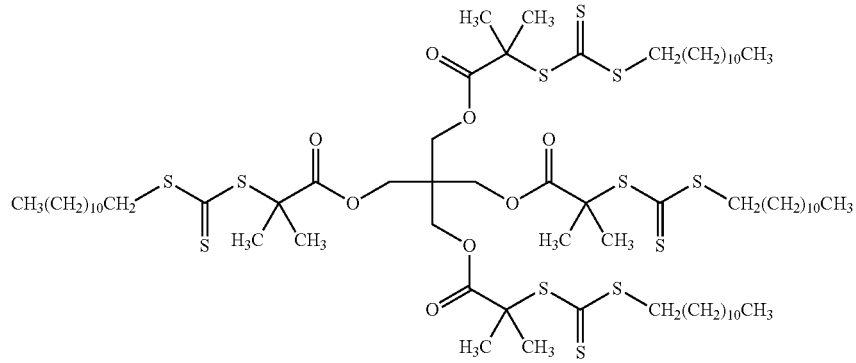

(an example of a 4-arm dendritic RAFT agent).

An example of the dendritic RAFT agent including a phosphazene ring as the central molecule/compound is:

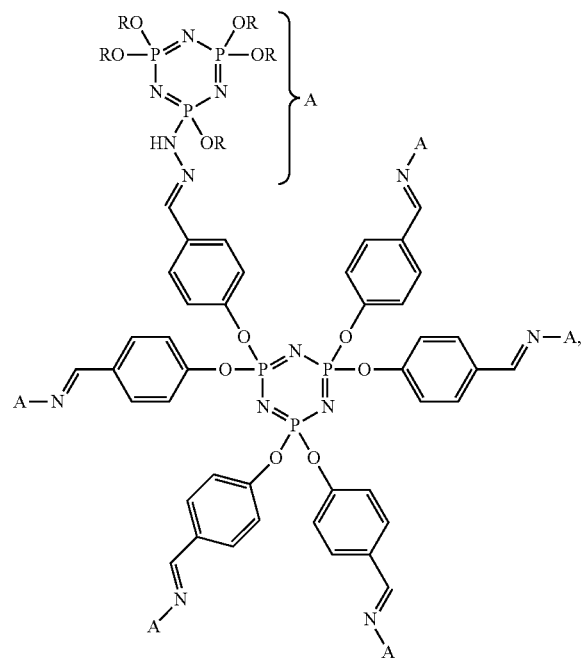

where each R is a trithiocarbonyl group. This is one example of dendritic RAFT agent including 30 arms.

To generate any example of the homopolymer disclosed herein, the desired monomer is polymerized in the presence of the RAFT agent or the dendritic RAFT agent. To generate any example of the copolymer or the terpolymer disclosed herein, a mixture of the desired monomers is polymerized in the presence of the RAFT agent or the dendritic RAFT agent.

To generate some examples of the polymer including the tetrazine functional group, a first monomer including an activated ester or an amine functional group is polymerized in the presence of the RAFT agent or the dendritic RAFT agent, and then the activated ester or the amine functional group is replaced with the tetrazine functional group. For the replacement reaction, 1 to 2 equivalents of the monomer including the tetrazine functional group is added to the polymer including the activated ester or amine functional group in a suitable solvent and catalyst (e.g., tetrahydrofuran/triethylamine (THF/Et$_3$N)) and reacted at room temperature for a time ranging from about 1 hour to about 6 hours.

The monomer or the mixture of the monomers may be incorporated into a liquid, such as water and a co-solvent (e.g., N-methyl-2-pyrollidone (NMP), dimethyl formamide (DMF), dimethyl sulfoxide (DMSO), acetonitrile (MeCN), methanol (MeOH), ethanol (EtOH), isopropyl alcohol (IPA), dioxane, acetone, dimethylacetamide (DMAc), or the like). The liquid containing the monomer or mixture of monomers may also include a buffer to at least substantially prevent undesirable changes in the pH. The pH of the mixture may be acidic (<7). Examples of suitable buffers include TRIS (tris(hydroxymethyl)aminomethane or TRIZMA®), Bis-tris methane buffer, ADA buffer (a zwitterionic buffering agent), MES (2-ethanesulfonic acid), MOPS (3-(N-morpholino) propanesulfonic acid), or another acidic buffer.

The polymerization reaction may take place at a temperature ranging from about 50° C. to about 80° C. for a time ranging from about 1 hour to about 48 hours. An initiator, including azo initiators, such as azobisisobutyronitrile (AIBN) or 2,2'-Azobis[2-(2-imidazolin-2-yl)propane]dihydrochloride (one commercially available example is VA-044 from FujiFilm), may also be included in the liquid with the monomer or mixture of monomers.

When two or more monomers are used, the process may incorporate the monomers randomly along the linear chain or into each of the arms. Other monomer incorporation scenarios are possible, such as statistical, alternating, etc. With statistical incorporation, the sequential distribution of the monomeric units obeys known statistical laws. With alternating incorporation, the monomeric units are incorporated that they are alternating along the length.

When copolymers are to be generated, the mole ratio of the first monomer to the second monomer may range from about 1:1 to about 1:49. As one example, a copolymer may include from about 2 mol % to about 50 mol % of the monomer containing the azide and from about 50 mol % to about 98 mol % of the monomer containing the acrylamide. When terpolymers are generated, the mole ratio of the first monomer to the second monomer to the third monomer may range from about 1:1:48 to about 2:5:3. As one example, a terpolymer may include from about 2 mol % to about 20 mol % of the monomer containing the tetrazine, from about 2 mol % to about 50 mol % of the monomer containing the azide, and from about 30 mol % to about 96 mol % of the monomer containing the acrylamide.

In other example copolymers and terpolymers, the monomers may be incorporated along the linear chain or into each of the arms in controlled blocks. In this example, the block copolymer may be formed in the presence of the RAFT agent or the dendritic RAFT agent. One example of this method involves polymerizing a first block with a first monomer in the presence of the RAFT agent or the dendritic RAFT agent to form an intermediate polymer (which includes the first block); and then polymerizing a second block with a second monomer in the presence of the intermediate polymer to form an example of the polymer (which includes both blocks along the linear chain or into each of the arms). This process may be repeated with another monomer if a third block is desired.

It may also be desired to perform end group modification, e.g., to remove the thiocarbonylthio group. Examples of suitable end group modification techniques include end group thermolysis, radical induced reduction, hetero-Diels-Alder reactions, and reaction with nucleophiles. In one example, cleavage of the thiocarbonylthio group with hydrogen peroxide introduced hydroxyl end groups. In another example, cleavage of the thiocarbonylthio group by reduction introduces thiols which can becomes trapped by unused monomers to introduce end groups based on the monomer structure (e.g., a methacrylamide).

While RAFT polymerization has been described in detail, it is to be understood that other polymerization processes may be used.

Atom transfer radical polymerization (ATRP) is one example of another suitable polymerization technique. Examples of suitable ATRP mono-initiators that may be used to generate linear polymers include 2-azidoethyl 2-bromoisobutyrate, poly(ethylene glycol) methyl ether 2-bromoisobutyrate (of varying molecular weights), 2-(2-Bromoisobutyryloxy)ethyl methacrylate, Dodecyl 2-bromoisobutyrate, 2-Hydroxyethyl 2-bromoisobutyrate, 1-(Phthalimidomethyl) 2-bromoisobutyrate, Propargyl 2-bromoisobutyrate, or the like. These mono-initiators may alternatively be attached to any example of the central molecules/compounds disclosed herein to form a dendritic ATRP agent including the atom transfer radical polymerization (ATRP) initiator in each arm. A dendritic ATRP agent may include an ATRP initiator in each arm, and may have from 2 arms to 30 arms. In still other examples, the central molecules/compound itself is a multi-functional ATRP initiator. Some examples of these dendritic ATRP agents may be selected from the group consisting of Bis[2-(2'-bromoisobutyryloxy)ethyl]disulfide, 2-Bromoisobutyric anhydride, Ethylene bis(2-bromoisobutyrate), Pentaerythritol tetrakis(2-bromoisobutyrate), Dipentaerythritol hexakis(2-bromoisobutyrate), and 1,1,1-Tris(2-bromoisobutyryloxymethyl)ethane.

Nitroxide (aminooxyl) mediated polymerization (NMP) is another example of a suitable polymerization technique. Examples of suitable NMP mono-initiators that may be used to generate linear polymers include

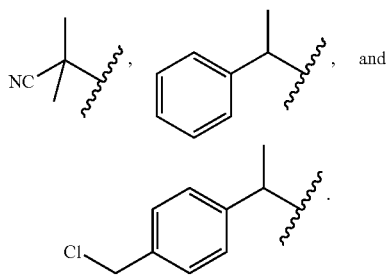

It is to be understood that any nitroxide end group(s) may be attached to the NMP mono-initiator, such as 2,2,6,6-Tetramethylpiperidin-1-yl)oxyl (TEMPO):

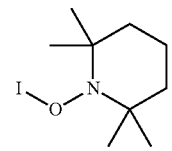

(where I is the mono-functional initiator), di-t-butyl nitroxide:

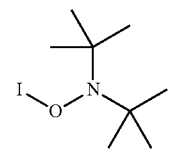

(where I is the mono-functional initiator), 1,1,3,3-tetraethylisoindolin-N-oxyl tetraethylisoindoline nitroxide:

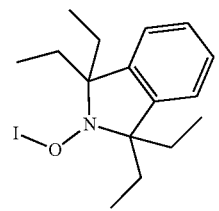 [SMILES: CCC1(CC)c2ccccc2C(CC)(CC)N1OI]

(where I is the mono-functional initiator), 2,2,5-Trimethyl-4-phenyl-3-azahexane-3-nitroxide (TIPNO):

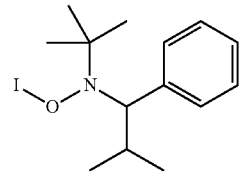 [SMILES: CC(C)C(c1ccccc1)N(OI)C(C)(C)C]

(where I is the mono-functional initiator), N-tert-butyl-N-[1-diethylphosphono-(2,2-dimethylpropyl)]nitroxide (SG1):

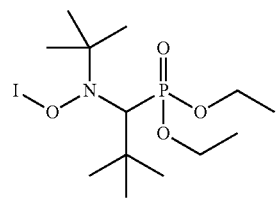 [SMILES: CCOP(=O)(OCC)C(N(OI)C(C)(C)C)C(C)(C)C]

(where I is the mono-functional initiator). These mono-initiators may alternatively be attached to any example of the central molecules/compounds disclosed herein to form a dendritic NMP agent including the NMP initiator in each arm.

Any of these mono-initiators may be attached to any example of the central molecules/compounds disclosed herein to form the dendritic agent including the NMP initiator in each arm. This particular dendritic agent is referred to herein as a dendritic NMP agent. The dendritic NMP agent includes an NMP initiator in each arm, and may have from 2 arms to 30 arms. In still other examples, the central molecules/compound itself is a multi-functional NMP initiator. Some examples of these dendritic NMP agents (multi-functional NMP initiators) may be:

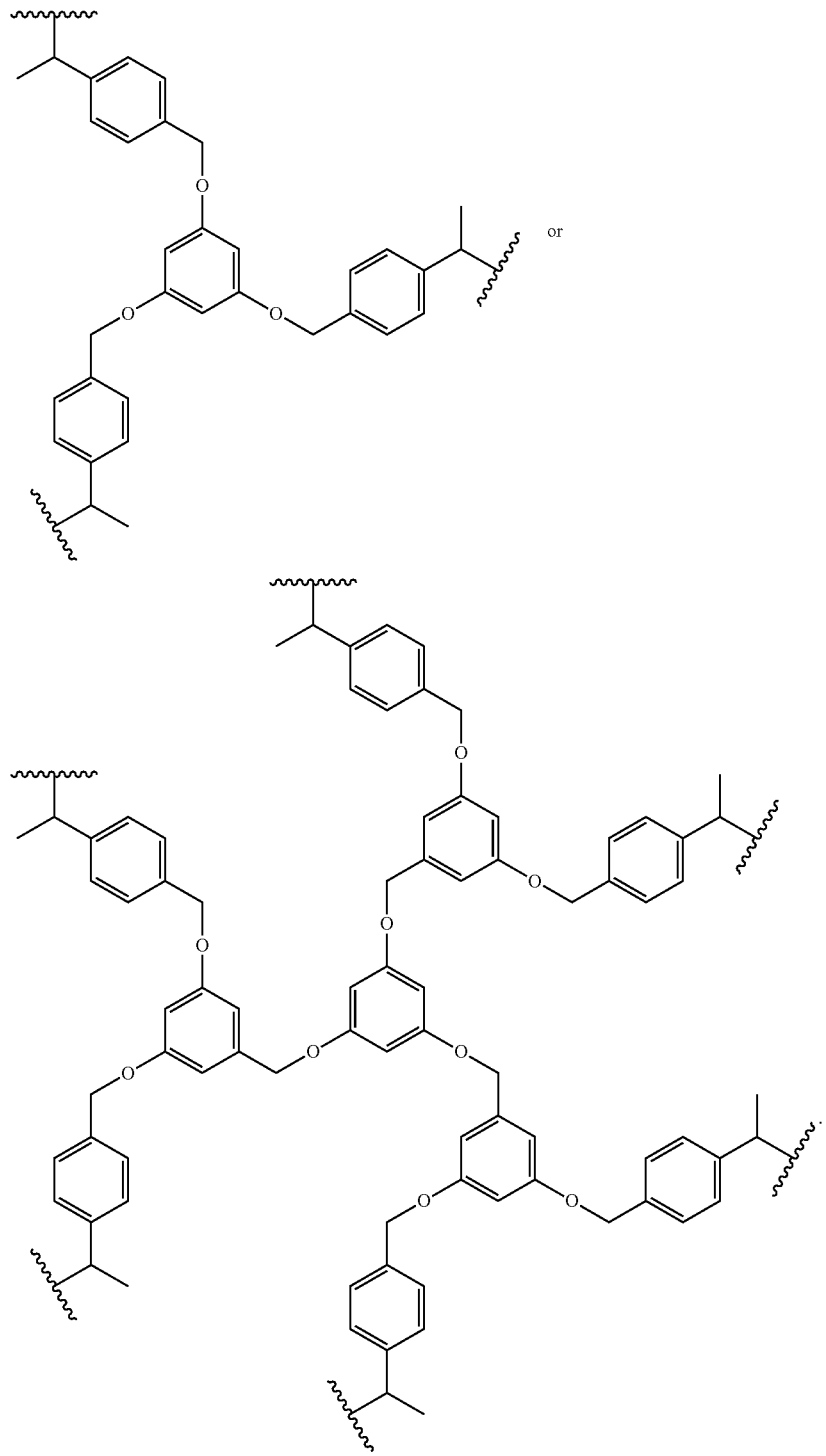

Any of the nitroxide end group(s) may be attached to each arm of these initiators. Specific examples of these dendritic NMP agents (multi-functional NMP initiators) include 1,3,5-tris((4-(1-((2,2,6,6-tetramethylpiperidin-1-yl)oxy)ethyl)benzyl)oxy)benzene:
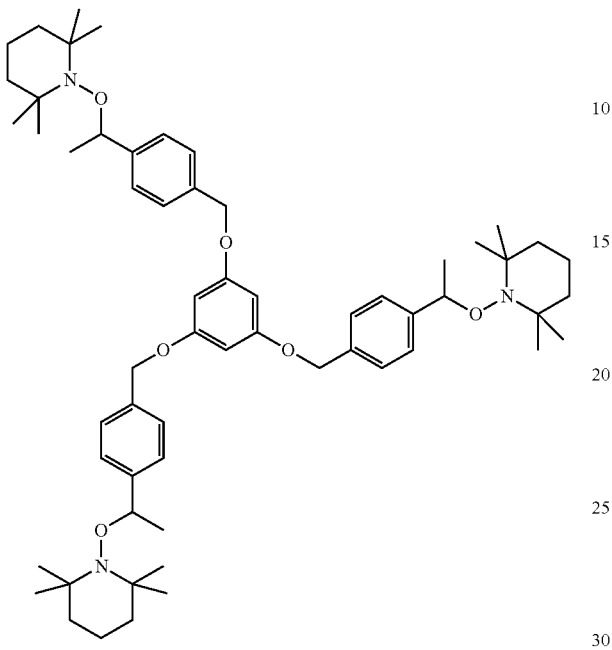
and 1,3,5-tris((3,5-bis((4-(1-((2,2,6,6-tetramethylpiperidin-1-yl)oxy)ethyl)benzyl)oxy)benzyl)oxy)benzene:
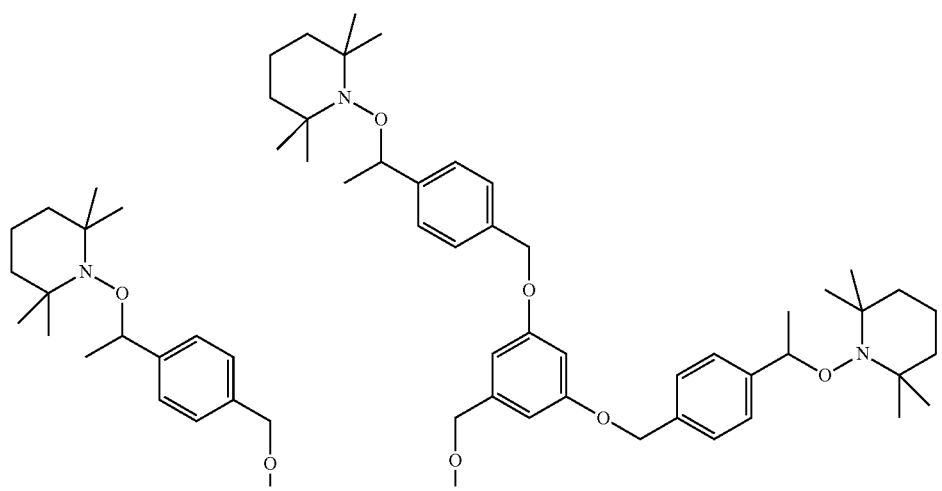

-continued

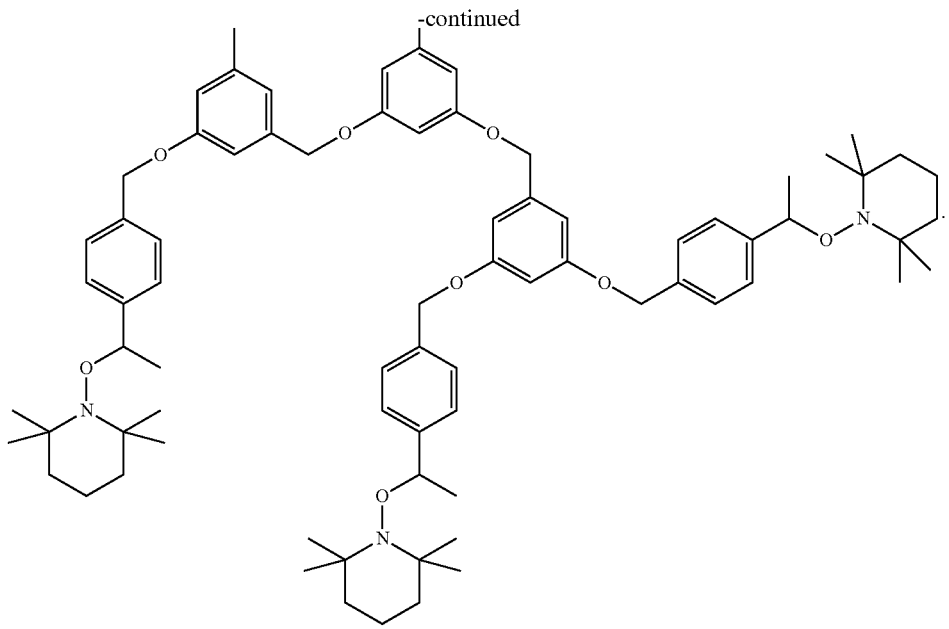

While RAFT polymerization, ATRP, or NMP polymerization may be used, it is to be understood that other polymerization processes may also be used. Other suitable polymerization processes include NMP polymerization in combination with RAFT or ATRP, NMP with an additional cross-linking step, cobalt-mediated polymerization, group transfer polymerization (GTP), ring opening polymerization (ROP), ionic polymerization, or any other polymerization process that either directly or indirectly yields the desired linear or multi-arm architecture.

Primer Sets

In the examples set forth herein, the flow cell includes one primer set attached to one of the polymers and a different primer set attached to another of the polymers.

Figure 1:
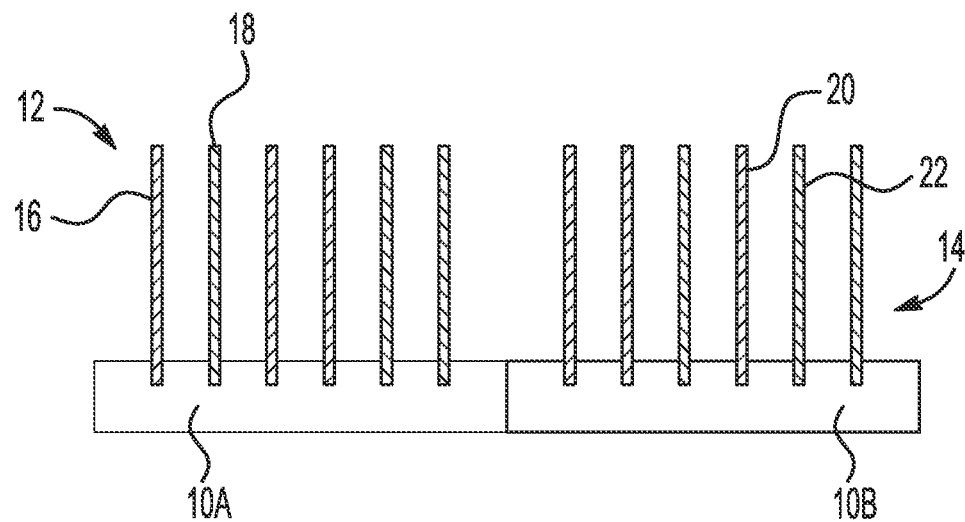
FIG. 1 is a schematic view of one example of orthogonal polymers and different primer sets respectively attached to the orthogonal polymers, where the different primer sets enable two different template strands to be amplified and clustered on adjacent orthogonal polymers.

In some examples, the different primer sets enable two different template strands to be amplified and clustered on adjacent orthogonal polymers. An example of these primers sets are shown in FIG. 1. The orthogonal polymers are shown at reference numerals 10A and 10B, one primer set 12 is shown attached to the first orthogonal polymer 10A, and the other primer set 14 is shown attached to the second orthogonal polymer 10B. As described herein, the orthogonal polymers 10A, 10B include different functional groups that can selectively react with the respective primer sets 12, 14.

In this example, the first primer set 12 includes two different primers 16, 18, such as forward and reverse amplification primers. The primers 16, 18 of the set 12 together enable the amplification of a library template having end adapters that are complementary to the two different primers 16, 18. The second primer set 14 also includes two different primers 20, 22 that enable the amplification of a different library template having end adapters that are complementary to the two different primers 20, 22.

As examples, the first primer set 12 includes P5 and P7 primers; and the second primer set 14 includes any combination of the PA primers, the PB primers, the PC primers, and the PD primers set forth herein. In other examples, P15 and P7 may be used in the first primer set 12. As examples, the second primer set 14 may include any two (or three) PA, PB, PC, and PD primers, or any combination of one PA primers and one PB, PC, or primer PD, or any combination of one PB primers and one PC or primer PD, or any combination of one PC primer and one primer PD. The PX primers described herein may be used as capture primers that seed a library template molecule, but that do not otherwise participate in amplification as they are orthogonal to all of the other primers. For sequential paired end sequencing using the primers sets 12, 14, different PX primers may be included with the first primer set 12 and the second primer set 14 to capture different library template molecules.

Examples of P5 and P7 primers are used on the surface of commercial flow cells sold by Illumina Inc. for sequencing, for example, on HISEQ™, HISEQX™, MISEQ™, MISEQDX™, MINISEQ™, NEXTSEQ™, NEXTSEQDX™, NOVASEQ™, ISEQ™, GENOME ANALYZER™, and other instrument platforms. The P5 primer is:

```
P5: 5' → 3'
                              (SEQ. ID. NO. 1)
AATGATACGGCGACCACCGAGAUCTACAC
```

The P7 primer may be any of the following:

```
P7 #1: 5' → 3'
                              (SEQ. ID. NO. 2)
CAAGCAGAAGACGGCATACGAnAT

P7 #2: 5' → 3'
                              (SEQ. ID. NO. 3)
CAAGCAGAAGACGGCATACnAGAT
``` where "n" is uracil or 8-oxoguanine in each of the sequences.

The P15 primer is:

```
P15: 5' → 3'
                              (SEQ. ID. NO. 4)
AATGATACGGCGACCACCGAGAnCTACAC
``` where "n" is allyl-T.

The other primers (PA-PD) mentioned above include:

```
PA 5' → 3'
                                    (SEQ. ID. NO. 5)
GCTGGCACGTCCGAACGCTTCGTTAATCCGTTGAG cPA (PA') 5' → 3'
                                    (SEQ. ID. NO. 6)
CTCAACGGATTAACGAAGCGTTCGGACGTGCCAGC

PB 5' → 3'
                                    (SEQ. ID. NO. 7)
CGTCGTCTGCCATGGCGCTTCGGTGGATATGAACT cPB (PB') 5' → 3'
                                    (SEQ. ID. NO. 8)
AGTTCATATCCACCGAAGCGCCATGGCAGACGACG

PC 5' → 3'
                                    (SEQ. ID. NO. 9)
ACGGCCGCTAATATCAACGCGTCGAATCCGCAACT cPC (PC') 5' → 3'
                                    (SEQ. ID. NO. 10)
AGTTGCGGATTCGACGCGTTGATATTAGCGGCCGT

PD 5' → 3'
                                    (SEQ. ID. NO. 11)
GCCGCGTTACGTTAGCCGGACTATTCGATGCAGC cPD (PD') 5' → 3'
                                    (SEQ. ID. NO. 12)
GCTGCATCGAATAGTCCGGCTAACGTAACGCGGC
```

While not shown in the example sequences for PA-PD, it is to be understood that any of these primers may include a cleavage site, such as uracil, 8-oxoguanine, allyl-T, etc. at any point in the strand.

The PX capture primers may be:

```
PX 5' → 3'
                                    (SEQ. ID. NO. 13)
AGGAGGAGGAGGAGGAGGAGGAGG cPX (PX') 5' → 3'
                                    (SEQ. ID. NO. 14)
CCTCCTCCTCCTCCTCCTCCTCCT
```

Each of the primers disclosed herein may also include a polyT sequence at the 5' end of the primer sequence. In some examples, the polyT region includes from 2 T bases to 20 T bases. As specific examples, the polyT region may include 3, 4, 5, 6, 7, or 10 T bases.

Figure 2A:
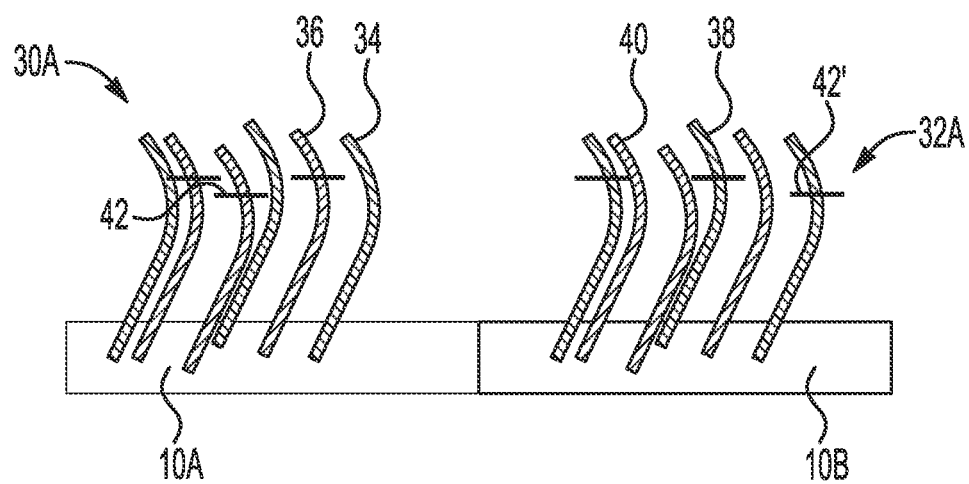
FIG. 2A through FIG. 2D are schematic views of different examples of first and second primer sets attached to the orthogonal polymers, where the different primer sets enable the generation of forward and reverse strands on the adjacent orthogonal polymers.
Figure 2B:
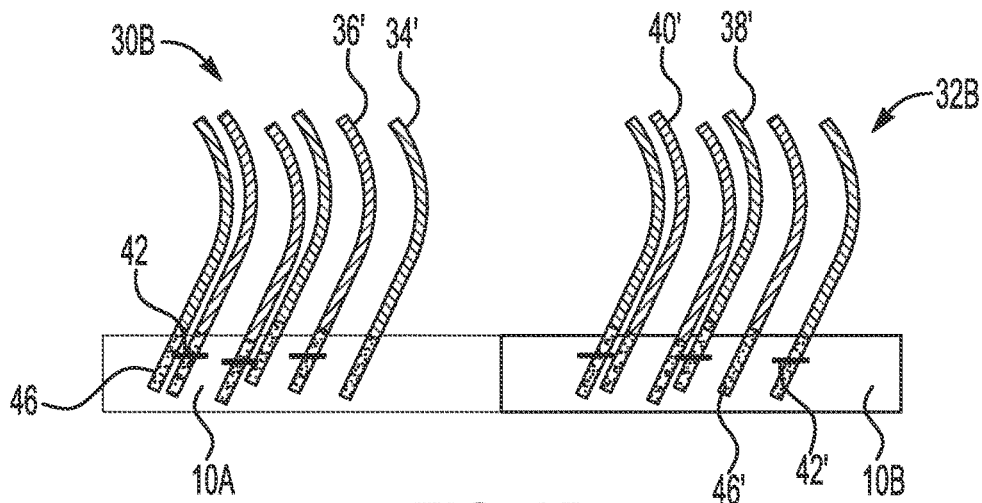
Figure 2C:
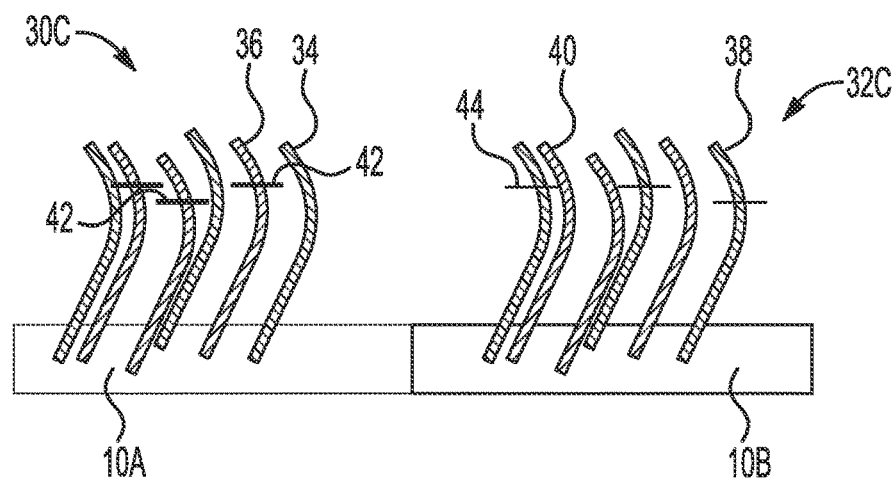
Figure 2D:
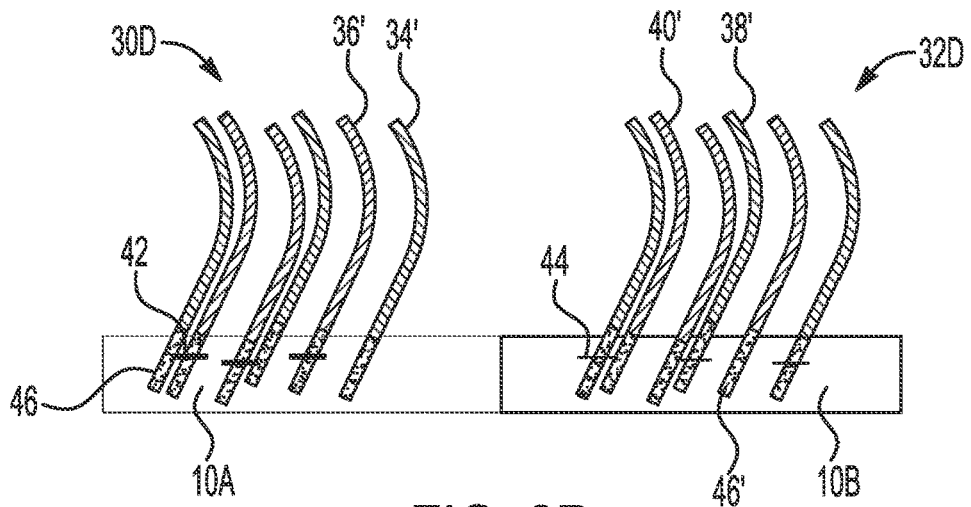

The 5' end of each primer may also include a linker (e.g., 46, 46' described in reference to FIG. 2B and FIG. 2D). Any linker that includes a terminal alkyne group or another suitable terminal functional group that can attach to the surface functional groups of the orthogonal polymers 10A, 10B may be used. In one example, the primers are terminated with hexynyl.

In other examples, the different primers sets are related in that one set includes an un-cleavable first primer and a cleavable second primer, and the other set includes a cleavable first primer and an un-cleavable second primer. These primer sets allow a single template strand to be amplified and clustered across both primer sets, and also enable the generation of forward and reverse strands on the adjacent orthogonal polymers due to the cleavage groups being present on the opposite primers of the sets. Examples of these primer sets will be discussed in reference to FIG. 2A through FIG. 2D.

FIG. 2A through FIG. 2D depict different configurations of the primer sets 30A, 32A, 30B, 32B, 30C, 32C, and 30D, 32D attached to the orthogonal polymers 10A, 10B.

Each of the first primer sets 30A, 30B, 30C, and 30D includes an un-cleavable first primer 34 or 34' and a cleavable second primer 36 or 36'; and each of the second primer sets 32A, 32B, 32C, and 32D includes a cleavable first primer 38 or 38' and an un-cleavable second primer 40 or 40'.

The un-cleavable first primer 34 or 34' and the cleavable second primer 36 or 36' are oligonucleotide pairs, e.g., where the un-cleavable first primer 34 or 34' is a forward amplification primer and the cleavable second primer 36 or 36' is a reverse amplification primer or where the cleavable second primer 36 or 36' is the forward amplification primer and the un-cleavable first primer 34 or 34' is the reverse amplification primer. In each example of the first primer set 30A, 30B, 30C, and 30D the cleavable second primer 36 or 36' includes a cleavage site 42, while the un-cleavable first primer 34 or 34' does not include a cleavage site 42.

The cleavable first primer 38 or 38' and the un-cleavable second primer 40 or 40' are also oligonucleotide pairs, e.g., where the cleavable first primer 38 or 38' is a forward amplification primer and the un-cleavable second primer 40 or 40' is a reverse amplification primer or where the un-cleavable second primer 40 or 40' is the forward amplification primer and the cleavable first primer 38 or 38' is the reverse amplification primer. In each example of the second primer set 32A, 32B, 32C, and 32D, the cleavable first primer 38 or 38' includes a cleavage site 42' or 44, while the un-cleavable second primer 40 or 40' does not include a cleavage site 42' or 44.

It is to be understood that the un-cleavable first primer 34 or 34' of the first primer set 30A, 30B, 30C, and 30D and the cleavable first primer 38 or 38' of the second primer set 32A, 32B, 32C, and 32D have the same nucleotide sequence (e.g., both are forward amplification primers), except that the cleavable first primer 38 or 38' includes the cleavage site 42' or 44 integrated into the nucleotide sequence or into a linker 46' attached to the nucleotide sequence. Similarly, the cleavable second primer 36 or 36' of the first primer set 30A, 30B, 30C, and 30D and the un-cleavable second primer 40 or 40' of the second primer set 32A, 32B, 32C, and 32D have the same nucleotide sequence (e.g., both are reverse amplification primers), except that the cleavable second primer 36 or 36' includes the cleavage site 42 integrated into the nucleotide sequence or into a linker 46 attached to the nucleotide sequence.

It is to be understood that when the first primers 34 and 38 or 34' and 38' are forward amplification primers, the second primers 36 and 40 or 36' and 40' are reverse primers, and vice versa.

The un-cleavable primers 34, 40 or 34', 40' may be any primers with a universal sequence for capture and/or amplification purposes, such as the P5 and P7 primers or any combination of the PA, PD, PC, PD primers (e.g., PA and PB or PA and PD, etc.). In some examples, the P5 and P7 primers are un-cleavable primers 34, 40 or 34', 40' because they do not include a cleavage site 42, 42', 44. Thus, P5 in SEQ. ID. NO. 1 would not include the uracil and P7 in SEQ. ID. NO. 2 or SEQ. ID. NO. 3 would not include the 8-oxoguanine. It is to be understood that any suitable universal sequence can be used as the un-cleavable primers 34, 40 or 34', 40'.

Examples of cleavable primers 36, 38 or 36', 38' include the P5 and P7 primers or other universal sequence primers (e.g., the PA, PB, PC, PD primers) with the respective cleavage sites 42, 42', 44 incorporated into the respective nucleic acid sequences (e.g., FIG. 2A and FIG. 2C), or into a linker 46', 46 that attaches the cleavable primers 36, 38 or 36', 38' to the respective orthogonal polymer 10A, 10B (FIG. 2B and FIG. 2D). Examples of suitable cleavage sites 42, 42', 44 include enzymatically cleavable nucleobases or chemically cleavable nucleobases, modified nucleobases, or linkers (e.g., between nucleobases), as described herein.

Each primer set 30A and 32A or 30B and 32B or 30C and 32C or 30D and 32D is attached to a respective orthogonal polymer 10A, 10B. As described herein, the orthogonal polymers 10A, 10B include different functional groups that can selectively react with the respective primers 34, 36 or 34', 36' or 38, 40 or 38', 40'.

While not shown in FIG. 2A through FIG. 2D, it is to be understood that one or both of the primer sets 30A, 30B, 30C, 30D or 32A, 32B, 32C or 32D may also include a PX primer for capturing a library template seeding molecule. As one example, PX may be included with the primer set 30A, 30B, 30C, 30D, but not with primer set 32A, 32B, 32C or 32D. As another example, PX may be included with the primer set 30A, 30B, 30C, 30D and with the primer set 32A, 32B, 32C or 32D. The density of the PX motifs should be relatively low in order to minimize polyclonality within each depression 54.

FIG. 2A through FIG. 2D depict different configurations of the primer sets 30A, 32A, 30B, 32B, 30C, 32C, and 30D, 32D attached to the orthogonal polymers 10A, 10B. More specifically, FIG. 2A through FIG. 2D depict different configurations of the primers 34, 36 or 34', 36' and 38, 40 or 38', 40' that may be used.

In the example shown in FIG. 2A, the primers 34, 36 and 38, 40 of the primer sets 30A and 32A are directly attached to the orthogonal polymers 10A, 10B, for example, without a linker 46, 46'. The orthogonal polymer 10A has surface functional groups that can immobilize the terminal groups at the 5' end of the primers 34, 36. Similarly, the orthogonal polymer 10B has surface functional groups that can immobilize the terminal groups at the 5' end of the primers 38, 40. As described, the immobilization chemistry between the orthogonal polymer 10A and the primers 34, 36 and the immobilization chemistry between the orthogonal polymer 10B and the primers 38, 40 is different so that the primers 34, 36 or 38, 40 selectively attach to the desirable polymer 10A, 10B. The polymer 10A, 10B may include any example of the functional group pairs as described herein. For example, the polymer 10A may include an activated ester that can graft an amine-terminated primer, and the polymer 10B may include an azide that can graft an alkyne-terminated primer. For another example, the polymer 10A may include a tetrazine that can graft a BCN- or norbornene-terminated primer, and the polymer 10B may include an activated ester that can graft an amine-terminated primer. For still another example, the polymer 10A may include an azide that can graft an alkyne-terminated primer, and the polymer 10B may include an aryl-iodide that can graft a boronic acid-terminated primer. For yet another example, the polymer 10A may include a tetrazine that can graft a norbornene-terminated primer, and the polymer 10B may include an azide that can graft an alkyne-terminated primer. In any of these examples, immobilization may be by single point covalent attachment to the respective polymer 10A, 10B at the 5' end of the respective primers 34 and 36 or 38 and 40.

Also, in the example shown in FIG. 2A, the cleavage site 42, 42' of each of the cleavable primers 36, 38 is incorporated into the sequence of the primer. In this example, the same type of cleavage site 42, 42' is used in the cleavable primers 36, 38 of the respective primer sets 30A, 32A. As an example, the cleavage sites 42, 42' are uracil bases, and the cleavable primers 36, 38 are P5U and P7U. The uracil bases or other cleavage sites may also be incorporated into any of the PA, PB, PC, and PD primers to generate the cleavable primers 36, 38. In this example, the un-cleavable primer 34 of the oligonucleotide pair 34, 36 may be P7, and the un-cleavable primer 40 of the oligonucleotide pair 38, 40 may be P5. Thus, in this example, the first primer set 30A includes P7, P5U and the second primer set 32A includes P5, P7U. The primer sets 30A, 32A have opposite linearization chemistries, which, after amplification, cluster generation, and linearization, allows forward template strands to be formed on one orthogonal polymer 10A and reverse strands to be formed on the other orthogonal polymer 10B.

In the example shown in FIG. 2B, the primers 34', 36' and 38', 40' of the primer sets 30B and 32B are attached to the orthogonal polymers 10A, 10B, for example, through linkers 46, 46'. The orthogonal polymers 10A, 10B include respective functional groups of the functional group pairs disclosed herein, and the terminal ends of the respective linkers 46, 46' are capable of covalently attaching to the respective functional groups. As such, the orthogonal polymer 10A may have surface functional groups that can immobilize the linker 46 at the 5' end of the primers 34', 36'. Similarly, the orthogonal polymer 10B may have surface functional groups that can immobilize the linker 46' at the 5' end of the primers 38', 40'. The immobilization chemistry for the orthogonal polymer 10A and the linkers 46 and the immobilization chemistry for the orthogonal polymer 10B and the linkers 46' is different so that the primers 34', 36' or 38', 40' selectively graft to the desirable orthogonal polymer 10A, 10B.

Examples of suitable linkers 46, 46' may include nucleic acid linkers (e.g., 10 nucleotides or less) or non-nucleic acid linkers, such as a polyethylene glycol chain, an alkyl group or a carbon chain, an aliphatic linker with vicinal diols, a peptide linker, etc. An example of a nucleic acid linker is a polyT spacer, although other nucleotides can also be used. In one example, the spacer is a 6T to 10T spacer. The following are some examples of nucleotides including non-nucleic acid linkers with terminal alkyne groups (where B is the nucleobase and "oligo" is the primer):

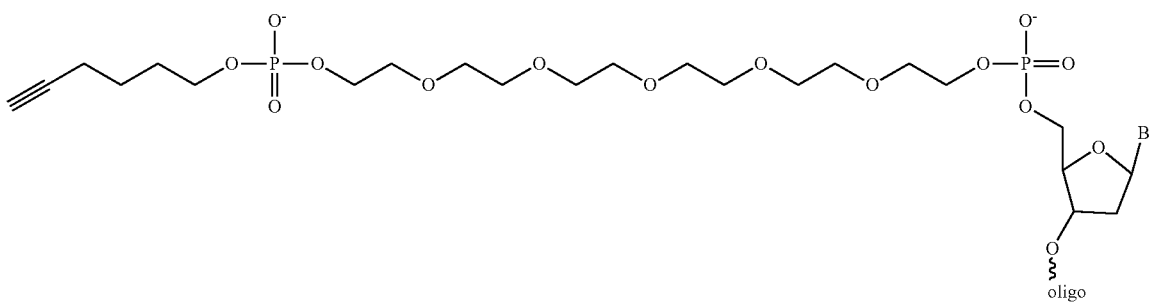

5' Hexynyl-HEG-oligo

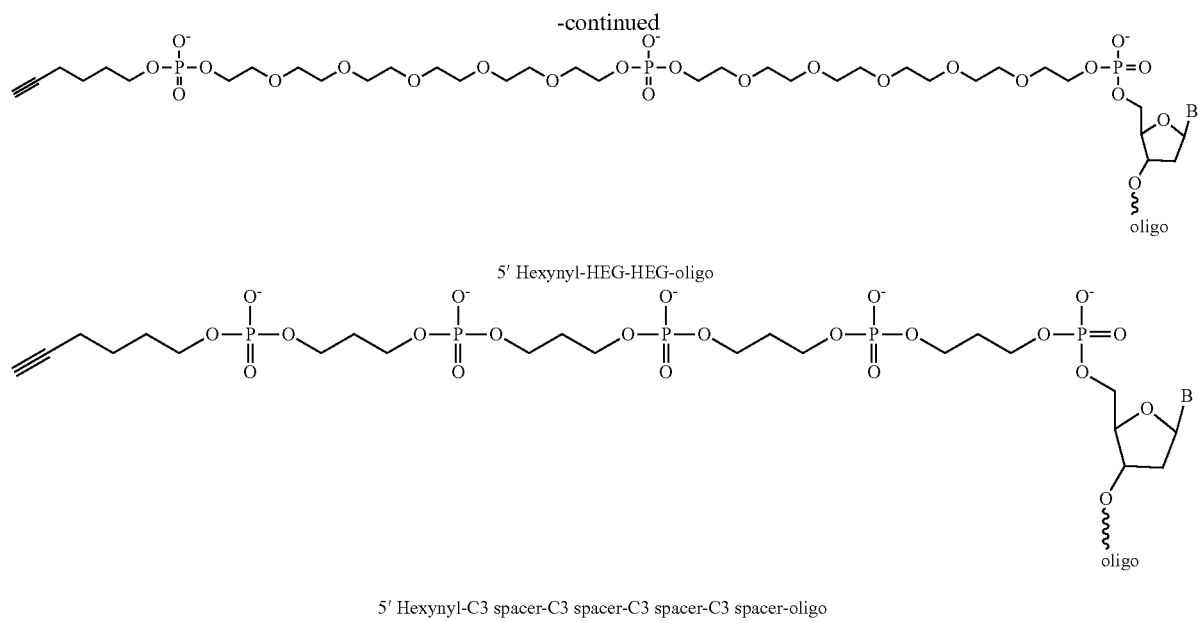

5' Hexynyl-HEG-HEG-oligo

5' Hexynyl-C3 spacer-C3 spacer-C3 spacer-C3 spacer-oligo

In the example shown in FIG. 2B, the primers 34', 38' have the same sequence (e.g., P5 without the uracil) and the same or different linker 46, 46'. The primer 34' is uncleavable, whereas the primer 38' includes the cleavage site 42' incorporated into the linker 46'. Also in this example, the primers 36', 40' have the same sequence (e.g., P7 without "n") and the same or different linker 46, 46'. The primer 40' in un-cleavable, and the primer 36' includes the cleavage site 42 incorporated into the linker 46. The same type of cleavage site 42, 42' is used in the linker 46, 46' of each of the cleavable primers 36', 38'. As an example, the cleavage sites 42, 42' may be uracil bases that are incorporated into nucleic acid linkers 46, 46'. The primer sets 30B, 32B have opposite linearization chemistries, which, after amplification, cluster generation, and linearization, allows forward template strands to be formed on one orthogonal polymer 10A and reverse strands to be formed on the other orthogonal polymer 10B.

The example shown in FIG. 2C is similar to the example shown in FIG. 2A, except that different types of cleavage sites 42, 44 are used in the cleavable primers 36, 38 of the respective primer sets 30C, 32C. As examples, two different enzymatic cleavage sites may be used, two different chemical cleavage sites may be used, or one enzymatic cleavage site and one chemical cleavage site may be used. Examples of different cleavage sites 42, 44 that may be used in the respective cleavable primers 36, 38 include any combination of the following: vicinal diol, uracil, allyl ether, disulfide, restriction enzyme site, and 8-oxoguanine.

The example shown in FIG. 2D is similar to the example shown in FIG. 2B, except that different types of cleavage sites 42, 44 are used in the linkers 46, 46' attached to the cleavable primers 36', 38' of the respective primer sets 30D, 32D. Examples of different cleavage sites 42, 44 that may be used in the respective linkers 46, 46' attached to the cleavable primers 36', 38' include any combination of the following: vicinal diol, uracil, allyl ether, disulfide, restriction enzyme site, and 8-oxoguanine.

In any of the examples shown in FIG. 1 and FIG. 2A through FIG. 2D, the attachment of the primers 16, 18 and 20, 22, or 34, 36 and 38, 40 or 34', 36' and 38', 40' to the orthogonal polymers 10A, 10B leaves a template-specific portion of the primers 16, 18 and 20, 22, or 34, 36 and 38, 40 or 34', 36' and 38', 40' free to anneal to its cognate template and the 3' hydroxyl group free for primer extension.

As will be described in more detail below, the primers 16, 18 and 20, 22, or 34, 36 and 38, 40 or 34', 36' and 38', 40' may be attached to the respective orthogonal polymer 10A, 10B prior to its application to a flow cell substrate, and thus the orthogonal polymers 10A, 10B may be pre-grafted. In other examples, the primers 16, 18 and 20, 22, or 34, 36 and 38, 40 or 34', 36' and 38', 40' may be attached to the respective orthogonal polymer 10A, 10B after its application to the flow cell substrate.

Flow Cell Architecture

The orthogonal polymers 10A, 10B and the different primer sets 12, 14, or 30A, 32A, or 30B, 32B, or 30C, 32C, or 30D, 32D may be used to define the sequencing surface chemistry within a flow cell.

In the examples disclosed herein, the flow cell includes a substrate; a pattern of two different silanes on at least a portion of a surface of the substrate; a first polymer (e.g., orthogonal polymer 10A) attached to a first of the two different silanes; a second polymer (e.g., orthogonal polymer 10B) attached to a second of the two different silanes, the first and second polymers 10A, 10B respectively including a first functional group and a second functional group of a functional group pair, the functional group pair being selected from the group consisting of an activated ester functional group and an azide functional group, a tetrazine functional group and an activated ester functional group, and a tetrazine functional group and an azide functional group; a first primer set (e.g., 12, 30A, 30B, 30C, or 30D) grafted to the first polymer; and a second primer set (e.g., 14, 32A, 32B, 32C, or 32D) grafted to the second polymer, wherein the first and second primer sets are different. The flow cell and examples of the architecture within the flow cell will be described in reference to FIG. 3A through FIG. 3C.

Figure 3A:
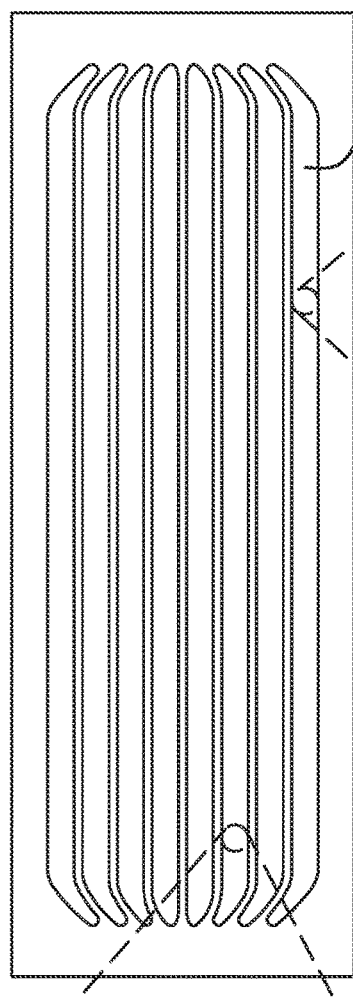
FIG. 3A is a top view of an example of a flow cell.

One example of the flow cell 50 is shown in FIG. 3A from a top view. The flow cell 50 may include two patterned structures bonded together or one patterned structure bonded to a lid. Between the two patterned structures or the one patterned structure and the lid is a flow channel 52. The example shown in FIG. 3A incudes eight flow channels 52. While eight flow channels 52 are shown, it is to be understood that any number of flow channels 52 may be included in the flow cell 50 (e.g., a single flow channel 52, four flow channels 52, etc.). Each flow channel 52 may be isolated from another flow channel 52 so that fluid introduced into the flow channel 52 does not flow into adjacent flow channel(s) 52. Some examples of the fluids introduced into the flow channel 52 may introduce reaction components (e.g., DNA sample, polymerases, sequencing primers, labeled nucleotides, etc.), washing solutions, deblocking agents, etc.

Figure 3B:
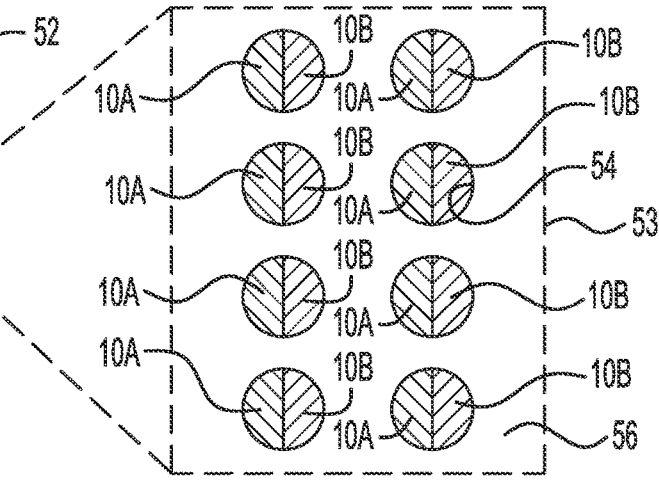
FIG. 3B and FIG. 3C are enlarged top views depicting different examples of the depressions in the flow channel of the flow cell, and the orthogonal polymers within the depressions.
Figure 3C:
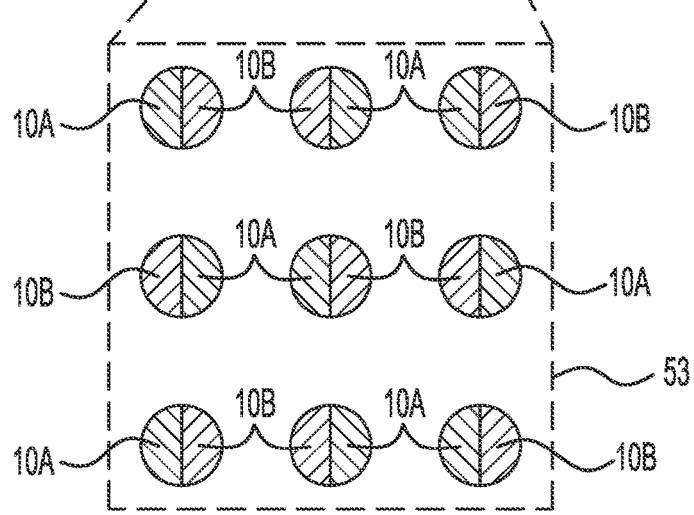

The flow channel 52 is at least partially defined by a patterned structure. The patterned structure may include a substrate, such as a single layer base support or a multi-layered structure. FIG. 3B and FIG. 3C depict a top view of the substrate 53, and thus depict the top of the single layer base support or the multi-layered structure.

Examples of suitable single layer base supports include epoxy siloxane, glass, modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon (polyamides), ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($Ta_2O_5$) or other tantalum oxide(s) ($TaO_x$), hafnium oxide ($HfO_2$), carbon, metals, inorganic glasses, or the like.

Examples of the multi-layered structure include the base support and at least one other layer on the base support. Some examples of the multi-layered structure include glass or silicon as the base support, with a coating layer (of tantalum oxide (e.g., tantalum pentoxide or another tantalum oxide(s) ($TaO_x$)) or another ceramic oxide at the surface. Other examples of the multi-layered structure include the base support (e.g., glass, silicon, tantalum pentoxide, or any of the other base support materials) and a patterned resin as the other layer. It is to be understood that any material that can be selectively deposited, or deposited and patterned to form depressions 54 (see FIG. 3B and FIG. 3C) and interstitial regions 56 may be used for the patterned resin.

As one example of the patterned resin, an inorganic oxide may be selectively applied to the base support via vapor deposition, aerosol printing, or inkjet printing. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

As another example of the patterned resin, a polymeric resin may be applied to the base support and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, etc. Some examples of suitable resins include a polyhedral oligomeric silsesquioxane resin based resin, an epoxy resin not based on a polyhedral oligomeric silsesquioxane, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (commercially available as POSS® from Hybrid Plastics) refers to a chemical composition that is a hybrid intermediate (e.g., $RSiO_{1.5}$) between that of silica ($SiO_2$) and silicone ($R_2SiO$). An example of a polyhedral oligomeric silsesquioxane may be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for POSS include epoxy, azide/azido, a thiol, a poly(ethylene glycol), a norbornene, a tetrazine, acrylates, and/or methacrylates, or further, for example, alkyl, aryl, alkoxy, and/or haloalkyl groups.

In an example, the single base support (whether used singly or as part of the multi-layered structure) may be a circular sheet, a panel, a wafer, a die etc. having a diameter ranging from about 2 mm to about 300 mm, e.g., from about 200 mm to about 300 mm, or may be a rectangular sheet, panel, wafer, die etc. having its largest dimension up to about 10 feet (~3 meters). For example, a die may have a width ranging from about 0.1 mm to about 10 mm. While example dimensions have been provided, it is to be understood that a single base support with any suitable dimensions may be used.

In an example, the flow channel 52 has a substantially rectangular configuration. The length and width of the flow channel 52 may be selected so a portion of the single base support or an outermost layer of the multi-layered structure surrounds the flow channel 52 and is available for attachment to a lid (not shown) or another patterned structure.

The depth of the flow channel 52 can be as small as a monolayer thick when microcontact, aerosol, or inkjet printing is used to deposit a separate material that defines the flow channel 52 walls. For other examples, the depth of the flow channel 52 can be about 1 µm, about 10 µm, about 50 µm, about 100 µm, or more. In an example, the depth may range from about 10 µm to about 100 µm. In another example, the depth may range from about 10 µm to about 30 µm. In still another example, the depth is about 5 µm or less. It is to be understood that the depth of the flow channel 52 may be greater than, less than or between the values specified above.

FIG. 3B and FIG. 3C depict examples of the architecture within the flow channel 52. Each of the architectures includes depressions 54 separated by interstitial regions 56, a pattern of two different silanes in each of the depressions 54, and the orthogonal polymers 10A, 10B respectively attached to the two different silanes within each of the depressions 54. While not shown, it is to be understood that different primer sets 12, 14, or 30A, 32A, or 30B, 32B, or 30C, 32C, or 30D, 32D respectively attach to the orthogonal polymers 10A, 10B.

Many different layouts of the depressions 54 may be envisaged, including regular, repeating, and non-regular patterns. In an example, the depressions 54 are disposed in a hexagonal grid for close packing and improved density. Other layouts may include, for example, rectangular layouts, triangular layouts, and so forth. In some examples, the layout or pattern can be an x-y format in rows and columns. In some other examples, the layout or pattern can be a repeating arrangement of the depressions 54 and the interstitial regions 56. In still other examples, the layout or pattern can be a random arrangement of the depressions 54 and the interstitial regions 56.

The layout or pattern may be characterized with respect to the density (number) of the depressions 54 in a defined area. For example, the depressions 54 may be present at a density of approximately 2 million per mm$^2$. The density may be tuned to different densities including, for example, a density of about 100 per mm$^2$, about 1,000 per mm$^2$, about 0.1 million per mm$^2$, about 1 million per mm$^2$, about 2 million per mm$^2$, about 5 million per mm$^2$, about 10 million per mm$^2$, about 50 million per mm$^2$, or more, or less. It is to be further understood that the density can be between one of the lower values and one of the upper values selected from the ranges above, or that other densities (outside of the given ranges) may be used. As examples, a high density array may be characterized as having depressions 54 separated by less than about 100 nm, a medium density array may be characterized as having the depressions 54 separated by about 400 nm to about 1 μm, and a low density array may be characterized as having the depressions 54 separated by greater than about 1 μm.

The layout or pattern of the depressions 54 may also or alternatively be characterized in terms of the average pitch, or the spacing from the center of one depression 54 to the center of an adjacent depression 54 (center-to-center spacing) or from the right edge of one depression 54 to the left edge of an adjacent depression 54 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 μm, about 0.5 μm, about 1 μm, about 5 μm, about 10 μm, about 100 μm, or more or less. The average pitch for a particular pattern of can be between one of the lower values and one of the upper values selected from the ranges above. In an example, the depressions 20 have a pitch (center-to-center spacing) of about 1.5 μm. While example average pitch values have been provided, it is to be understood that other average pitch values may be used.

The size of each depression 54 may be characterized by its volume, opening area, depth, and/or diameter. For example, the volume can range from about $1\times10^{-3}$ μm$^3$ to about 100 μm$^3$, e.g., about $1\times10^{-2}$ μm$^3$, about 0.1 μm$^3$, about 1 μm$^3$, about 10 μm$^3$, or more, or less. For another example, the opening area can range from about $1\times10^{-3}$ μm$^2$ to about 100 μm$^2$, e.g., about $1\times10^{-2}$ μm$^2$, about 0.1 μm$^2$, about 1 μm$^2$, at least about 10 μm$^2$, or more, or less. For still another example, the depth can range from about 0.1 μm to about 100 μm, e.g., about 0.5 μm, about 1 μm, about 10 μm, or more, or less. For yet another example, the diameter or length and width can range from about 0.1 μm to about 100 μm, e.g., about 0.5 μm, about 1 μm, about 10 μm, or more, or less.

Each of the architectures also includes the two different silanes (not shown). One of the silanes includes a functional group that can attach the first orthogonal polymer 10A (but not the second orthogonal polymer 10B), and the other of the silane includes a functional group that can attach the second orthogonal polymer 10B (but not the first orthogonal polymer 10A). In an example, the two different silanes are selected from the group consisting of an amino silane and an alkynyl silane, a norbornene silane and an amino silane, and a norbornene silane and an alkynyl silane. The amino silane and the alkynyl silane can respectively attach to an activated ester functional group and an azide functional group of the respective orthogonal polymers 10A, 10B. The norbornene silane and the amino silane can respectively attach to an azide functional group and an activated ester functional group of the respective orthogonal polymers 10A, 10B. The norbornene silane and the amino silane can respectively attach to a tetrazine functional group and an activated ester functional group of the respective orthogonal polymers 10A, 10B. The norbornene silane and the alkynyl silane can respectively attach to a tetrazine functional group and an azide functional group of the respective orthogonal polymers 10A, 10B.

An example of the amino silane may include (3-aminopropyl)trimethoxysilane) (APTMS), (3-aminopropyl)triethoxysilane) (APTES), N-(6-aminohexyl)aminomethyltriethoxysilane (AHAMTES), N-(2-aminoethyl)-3-aminopropyltriethoxysilane (AEAPTES), and N-(2-aminoethyl)-3-aminopropyltrimethoxysilane (AEAPTMS), each of which is available from Gelest.

The alkynyl silane may include a cycloalkyne unsaturated moiety, such as O-propargyl)-N-(triethoxysilylpropyl)carbamate, cyclooctyne, a cyclooctyne derivative, or bicyclononynes (e.g., bicyclo[6.1.0]non-4-yne or derivatives thereof, bicyclo[6.1.0]non-2-yne, or bicyclo[6.1.0]non-3-yne).

The norbornene silane may be a norbornene derivative, e.g., a (hetero)norbornene including an oxygen or nitrogen in place of one of the carbon atoms. An example of the norbornene silane includes [(5-bicyclo[2.2.1]hept-2-enyl) ethyl]trimethoxysilane.

The silanes may be deposited in a desired pattern within each of the depressions 54, so that the orthogonal polymers 10A, 10B (which selectively bond to the respective silanes) are applied in the desired pattern. The pattern of the silanes may be the same in each of the depressions 54 across the substrate 53, different in each of the depressions 54 across the substrate 53, or the same in some depressions 54 across the substrate 53 and different in other depressions 54 across the substrate 53. Examples of how the silanes are deposited in the desired pattern are described below in reference to FIG. 4A through FIG. 4H and FIG. 5A through FIG. 5H.

Each of the architectures also includes the orthogonal polymers 10A, 10B. Any of the orthogonal polymer sets disclosed herein may be included in each of the depressions 54. As examples, the polymer 10A may include the activated ester functional group and the polymer 10B may include the azide functional group; or the polymer 10A may include the tetrazine functional group and the polymer 10B may include the activated ester functional group; or the polymer 10A may include the tetrazine functional group and the polymer 10B may include the azide functional group. Any of the copolymers or terpolymers disclosed herein may also be used as long as the polymers 10A, 10B are orthogonal.

The position of the orthogonal polymers 10A, 10B within the depressions 54 is dictated by the pattern of the silanes within each depression 54.

The pattern of the orthogonal polymers 10A, 10B within each depression 54 may be repeated across the substrate 53, as shown in FIG. 3B and in FIG. 3C.

In the example shown in FIG. 3B, the pattern of the orthogonal polymers 10A, 10B is the same in each depression 54. In the example shown in FIG. 3B, the polymer 10A is on the left side of each depression 54 and the polymer 10B is on the right side of each depression 54. In other examples, the polymer 10B may be on the left side of each depression 54 and the polymer 10A may be on the right side of each depression 54; or the polymer 10A may be on the upper side of each depression 54 and the polymer 10B may be on the lower side of each depression 54; or the polymer 10B may be on the upper side of each depression 54 and the polymer 10A may be on the lower side of each depression 54.

In the example shown in FIG. 3C, different depressions 54 have different patterns of the orthogonal polymers 10A, 10B, but the patterns are repeated in an ordered fashion across the substrate 53. In the example shown in FIG. 3C, the rows and columns of depressions 54 alternate with one depression 54 having the polymer 10A on the left side of the depression 54 and the polymer 10B on the right side of depression 54, followed by a depression 54 having the polymer 10B on the left side of the depression 54 and the polymer 10A on the right side of depression 54, followed by a depression 54 having the polymer 10A on the left side of the depression 54 and the polymer 10B on the right side of depression 54, etc.

As noted above, in each example, the polymers 10A, 10B represent different areas that have different primer sets 12, 14, or 30A, 32A, or 30B, 32B, or 30C, 32C, or 30D, 32D respectively attached thereto.

Methods for Making the Flow Cells

The architecture within the flow cell 50 may be obtained through a variety of methods. Two examples of the method are shown in the schematic flow diagrams in FIG. 4A through FIG. 4H and in FIG. 5A through FIG. 5H. Another example of the method is shown in the flow diagram of FIG. 6.

The method shown in FIG. 4A through FIG. 4H and in FIG. 5A through FIG. 5H generally include generating a pattern of two different silanes 58A, 58B on at least a portion of a surface of a substrate 53; simultaneously depositing first and second polymers 10A, 10B, whereby the first polymer 10A attaches to a first of the two different silanes 58A and the second polymer 10B attaches to a second of the two different silanes 58B; and simultaneously grafting a first primer set 12 or 30A or 30B or 30C or 30D to the first polymer and a second primer set 14, or 32A, or 32B, or 32C, or 32D to the second polymer 10B, wherein the first and second primer sets 12, 14, or 30A, 32A, or 30B, 32B, or 30C, 32C, or 30D, 32D are different.

The method shown in FIG. 4A through FIG. 4H depicts one example for generating the pattern of the two different silanes 58A, 58B. This example method generally includes depositing the first 58A of the two different silanes 58A, 58B over the at least the portion of the surface of the substrate 53 (FIG. 4A); applying a photoresist 60 over the first of the two different silanes (FIG. 4B); developing the photoresist (generating insoluble portions 60') to define a pattern including an exposed portion 62 of the first 58A of the two different silanes and a covered portion 64 of the first 58A of the two different silanes 58A, 58B (FIG. 4C); removing the exposed portion 62 of the first 58A of the two different silanes 58A, 58B to reveal a corresponding exposed substrate portion 66 (FIG. 4D); depositing the second 58B of the two different silanes 58A, 58B over the corresponding exposed substrate portion 66 (FIG. 4D); and removing the photoresist 60' (FIG. 4E).

The substrate 53 shown in FIG. 4A through FIG. 4H is an example of the single layer base support having the depressions 54 defined therein.

As shown in FIG. 4A, the first 58A of the two different silanes 58A, 58B is applied over the surface of the substrate 53, including over the depressions 54 and the interstitial regions 56. Examples of suitable silane application methods include vapor deposition (e.g., a YES method), spin coating, or other deposition method disclosed herein.

The photoresist 60 is then applied on the first 58A of the two different silanes 58A, 58B, as shown in FIG. 4B. Any suitable deposition method set forth herein may be used to apply the photoresist 60. The development of the photoresist 60 to generate the insoluble portions 60' depends on the type of photoresist that is used.

Some examples utilize a negative photoresist. An example of a suitable negative photoresist includes the NR® series photoresist (available from Futurrex). Other suitable negative photoresists include the SU-8 Series and the KMPR® Series (both of which are available from Kayaku Advanced Materials, Inc.), or the UVN™ Series (available from DuPont). When the negative photoresist is used, it is selectively exposed to certain wavelengths of light to form the insoluble portions 60', and is exposed to a developer to remove soluble portions (e.g., those portions that are not exposed to the certain wavelengths of light). Examples of suitable developers for the negative photoresist include aqueous-alkaline solutions, such as diluted sodium hydroxide, diluted potassium hydroxide, or an aqueous solution of the metal ion free organic TMAH (tetramethylammoniumhydroxide).

In the example shown in FIG. 4C, the exposed portion 62 of the first 58A of the two different silanes 58A, 58B is revealed at an area where the negative photoresist is not exposed to light, is soluble in the developer, and thus is removed by the developer. In contrast, the covered portion 64 of the first 58A of the two different silanes is at an area where the negative photoresist is exposed to light to form insoluble portions 60', which are not soluble in, and thus not removed by, the developer.

Other examples utilize a positive photoresist. Examples of suitable positive photoresist includes the MICROPOSIT® S1800 series or the AZ® 1500 series, both of which are available from Kayaku Advanced Materials, Inc. Another example of a suitable positive photoresist is SPR™-220 (from DuPont). When the positive photoresist is used, selective exposure to certain wavelengths of light form a soluble region (e.g., which is at least 95% soluble in a developer), and the developer is used to remove the soluble regions. Those portions of the positive photoresist not exposed to light will become insoluble in the developer. Examples of suitable developers for the positive photoresist include aqueous-alkaline solutions, such as diluted sodium hydroxide, diluted potassium hydroxide, or an aqueous solution of the metal ion free organic TMAH (tetramethyl-ammoniumhydroxide).

In the example shown in FIG. 4C, the exposed portion 62 of the first 58A of the two different silanes 58A, 58B is revealed at an area where the positive photoresist is exposed to light, is soluble in the developer, and thus is removed by the developer. In contrast, the covered portion 64 of the first 58A of the two different silanes 58A, 58B is at an area where the positive photoresist is not exposed to light to form insoluble portions 60', which are not soluble in, and thus not removed by, the developer.

FIG. 4D illustrates i) the removal of the exposed portion 62 of the first 58A of the two different silanes 58A, 58B, which exposes a corresponding substrate portion 66; and ii) the application of the second 58B of the two different silanes 58A, 58B over the corresponding exposed substrate portion 66.

The exposed portion 62 of the first 58A of the two different silanes 58A, 58B is removed to reveal the corresponding exposed substrate portion 66 (FIG. 4D). Removal of the exposed portion 62 of the first 58A of the two different silanes 58A, 58B may involve chemical etching, dry etching, plasma treatment, etc. Chemical etching involves a solvent that can remove the silane 58A, but not the insoluble photoresist 60'. The insoluble photoresist 60' protects the underlying portion 64 of the first 58A of the two different silanes 58A, 58B during the removal of the exposed portion 62.

After removal of the exposed portion(s) 62, the second 58B of the two different silanes 58A, 58B is deposited over the corresponding exposed substrate portion 66. As depicted in FIG. 4D, the second 58B of the two different silanes 58A, 58B is also deposited over the insoluble photoresist 60'. Examples of suitable silane application methods include vapor deposition (e.g., a YES method), spin coating, or other deposition method disclosed herein.

The insoluble photoresist 60' is then removed, as depicted in FIG. 4E. The insoluble photoresist 60' may be lifted off with a remover, such as dimethylsulfoxide (DMSO), acetone, or an NMP (N-methyl-2-pyrrolidone) based stripper for an insoluble negative photoresist; or dimethylsulfoxide (DMSO), acetone, propylene glycol monomethyl ether acetate, or an NMP (N-methyl-2-pyrrolidone) based stripper for an insoluble positive photoresist. As shown in FIG. 4E, the lift-off process removes i) at least 99% of the insoluble photoresist 60' and ii) the second 58B of the two different silanes 58A, 58B thereon. The two different silanes 58A, 58B remain intact over the substrate 53. This process exposes each of the two different silanes 58A, 58B.

The process shown in FIG. 4A through FIG. 4E generates the pattern of the two different silanes 58A, 58B in each of the depressions 54. The development of the photoresist 60 enables one to control the pattern of the two different silanes 58A, 58B in each of the depressions 54.

After the pattern of the two different silanes 58A, 58B is generated, the orthogonal polymers 10A, 10B are simultaneously applied. Simultaneous deposition of the orthogonal polymers 10A, 10B may involve any suitable deposition technique that can apply both polymers 10A, 10B at the same time. Due to the functionality of the two different silanes 58A, 58B and the functional group pair of the orthogonal polymers 10A, 10B, the orthogonal polymers 10A, 10B are able to selectively attach to the respective silanes 58A, 58B. Thus, the orthogonal polymer 10A attaches to the silane 58A and the orthogonal polymer 10B attaches to the silane 58B. This is shown in FIG. 4F.

In FIG. 4G, the orthogonal polymer 10A that is attached to the silane 58A over the interstitial regions 56 is removed, e.g., using a polishing process. The polishing process may be performed with a chemical slurry (including, e.g., an abrasive, a buffer, a chelating agent, a surfactant, and/or a dispersant) which can remove the orthogonal polymer 10A, and in some instances the silane 58A, from the interstitial regions 56 without deleteriously affecting the underlying substrate 53 at those regions 56. Alternatively, polishing may be performed with a solution that does not include the abrasive particles.

The chemical slurry may be used in a chemical mechanical polishing system to polish the surface of the interstitial regions 56. The polishing head(s)/pad(s) or other polishing tool(s) is/are capable of polishing the orthogonal polymer 10A that may be present over the interstitial regions 56 while leaving the orthogonal polymers 10A, 10B in the depression(s) 54 at least substantially intact. As an example, the polishing head may be a Strasbaugh ViPRR II polishing head.

Cleaning and drying processes may be performed after polishing. The cleaning process may utilize a water bath and sonication. The water bath may be maintained at a relatively low temperature ranging from about 22° C. to about 30° C. The drying process may involve spin drying, or drying via another suitable technique.

As shown in FIG. 4H, the primer sets 12, 14, or 30A, 32A, or 30B, 32B, or 30C, 32C, or 30D, 32D are simultaneously grafted to the respective orthogonal polymers 10A, 10B. Simultaneous grafting of the primer sets 12, 14, or 30A, 32A, or 30B, 32B, or 30C, 32C, or 30D, 32D may involve flow through deposition (e.g., using a temporarily bound lid), dunk coating, spray coating, puddle dispensing, or by another suitable grafting method. Each of these example techniques may utilize a primer solution or mixture, which may include the primer(s) 16, 18, 20, 22 or 34, 36, 38, 40, or 34', 36', 38', 40', water, a buffer, and a catalyst. With any of the grafting methods, the primers 16, 18, or 34, 36, or 34', 36' attach to the orthogonal polymer 10A and have no affinity for the orthogonal polymer 10B or the interstitial regions 56; and the primers 20, 22 or 38, 40, or 38', 40' attach to the orthogonal polymer 10B and have no affinity for the orthogonal polymer 10A or the interstitial regions 56. The selective affinity is due to the functionality of the two different primer sets 12, 14, or 30A, 32A, or 30B, 32B, or 30C, 32C, or 30D, 32D and the functional group pair of the orthogonal polymers 10A, 10B.

Figure 5H:
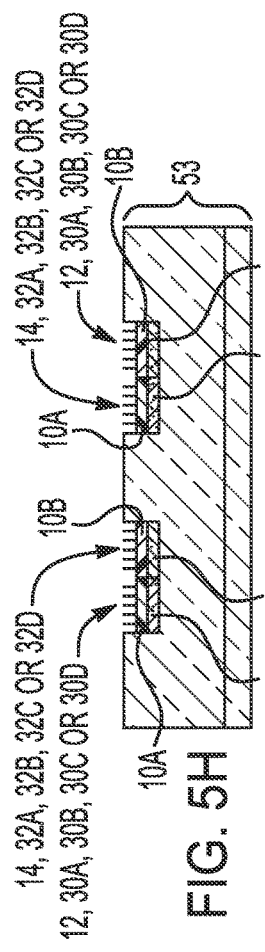
Figure 5G:
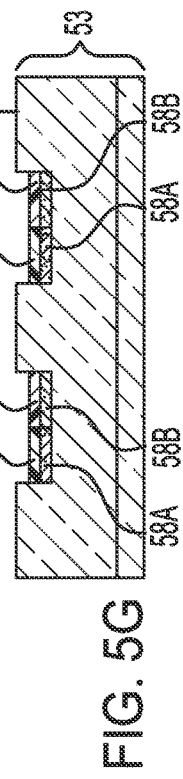
Figure 5F:
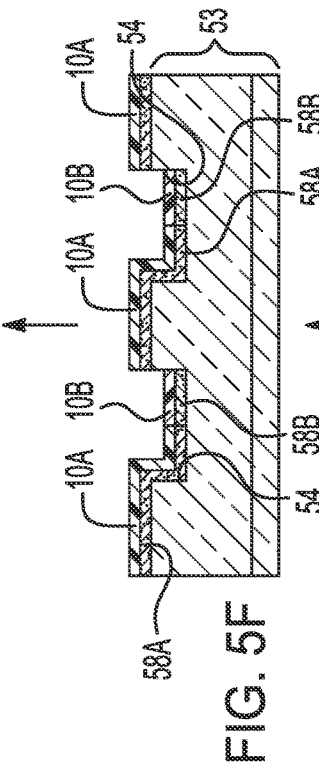
Figure 5E:
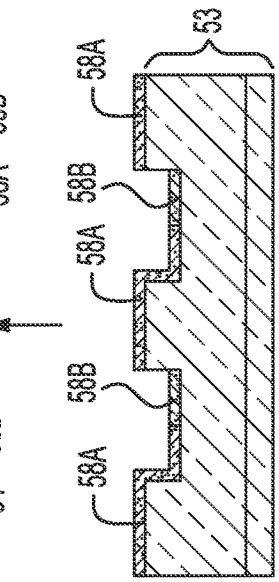

FIG. 5A through FIG. 5G depict another example for generating the pattern of the two different silanes 58A, 58B. This example method generally includes depositing the first 58A of the two different silanes 58A, 58B over the at least the portion of the surface of the substrate 53 (FIG. 5A); applying a photoresist 60 over the first 58A of the two different silanes 58A, 58B; developing the photoresist (generating insoluble portions 60') to define a pattern including an exposed portion 62 of the first 58A of the two different silanes 58A, 58B and a covered portion 64 of the first 58A of the two different silanes 58A, 58B (FIG. 5C); converting a functional group of the exposed portion 62 of the first 58A of the two different silanes 58A, 58B to form the second 58B of the two different silanes 58A, 58B (FIG. 5D); and removing the photoresist 60' (FIG. 5E).

The substrate 53 shown in FIG. 5A through FIG. 5H is an example of the multi-layered structure having the depressions 54 defined in a layer (e.g., a patterned resin) overlying a base support.

Figure 5A:
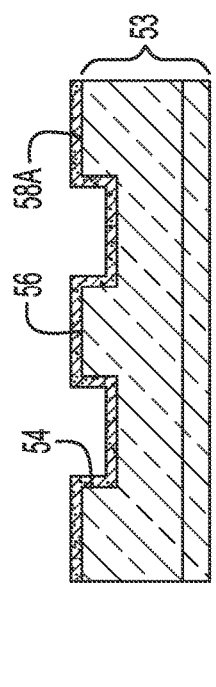

As shown in FIG. 5A, the first 58A of the two different silanes 58A, 58B is applied over the surface of the substrate 53, including over the depressions 54 and the interstitial regions 56. Examples of suitable silanes application methods include vapor deposition (e.g., a YES method), spin coating, or other deposition method disclosed herein.

Figure 5B:
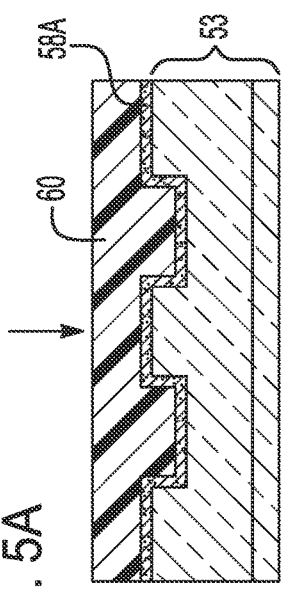

The photoresist 60 is then applied on the first 58A of the two different silanes 58A, 58B, as shown in FIG. 5B. Any suitable deposition method set forth herein may be used to apply the photoresist 60. The development of the photoresist 60 to generate the insoluble portions 60' depends on the type of photoresist that is used, as described in reference to FIG. 4B.

Figure 5C:
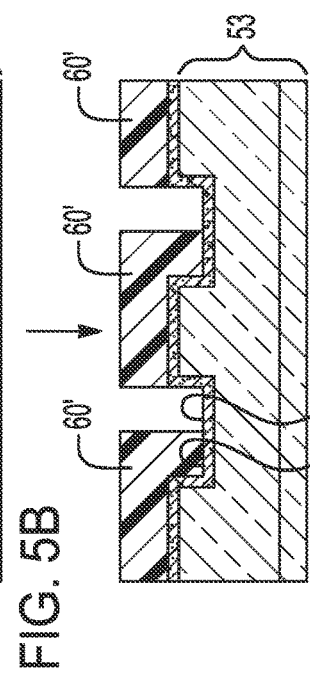

In the example shown in FIG. 5C, the exposed portion 62 of the first 58A of the two different silanes 58A, 58B is revealed at an area where a negative photoresist is not exposed to light, is soluble in the developer, and thus is removed by the developer. In contrast, the covered portion 64 of the first 58A of the two different silanes 58A, 58B is at an area where the negative photoresist is exposed to light to form insoluble portions 60', which are not soluble in, and thus not removed by, the developer.

Alternatively in the example shown in FIG. 4C, the exposed portion 62 of the first 58A of the two different silanes 58A, 58B is revealed at an area where a positive photoresist is exposed to light, is soluble in the developer, and thus is removed by the developer. In contrast, the covered portion 64 of the first 58A of the two different silanes 58A, 58B is at an area where the positive photoresist is not exposed to light to form insoluble portions 60', which are not soluble in, and thus not removed by, the developer.

Figure 5D:
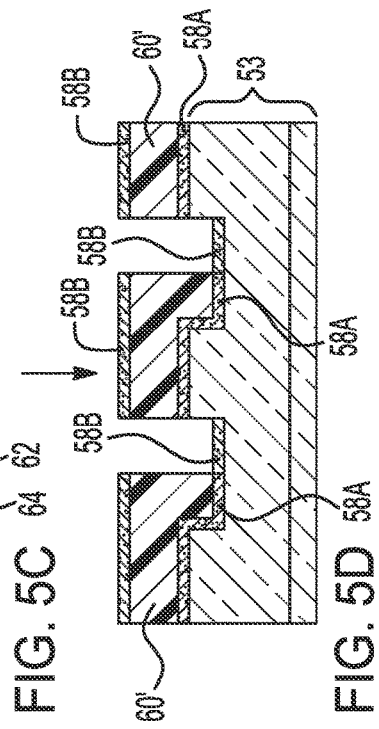

FIG. 5D illustrates the conversion of a functional group of the exposed portion 62 of the first 58A of the two different silanes 58A, 58B to form the second 58B of the two different silanes 58A, 58B. Additive free routes and/or any other technique that can replace the functional group of silane 58A to form silane 58B may be used. For example, with APTMS, NHS/EDC chemistry would be a desired option for the conversion. The insoluble photoresist 60' protects the underlying portion 64 of the first 58A of the two different silanes 58A, 58B during the functional group conversion of the exposed portion 62.

After the conversion of functional groups at the exposed portion(s) 62 to generate the second 58B of the two different silanes 58A, 58B, the insoluble photoresist 60' is then removed, as depicted in FIG. 5E. The insoluble photoresist 60' may be lifted off with a remover as described in reference to FIG. 4E. As shown in FIG. 5E, the lift-off process removes at least 99% of the insoluble photoresist 60'. The two different silanes 58A, 58B remain intact over the substrate 53. This process exposes each of the two different silanes 58A, 58B.

The process shown in FIG. 5A through FIG. 5E generates the pattern of the two different silanes 58A, 58B in each of the depressions 54. The development of the photoresist 60 enables one to control the pattern of the two different silanes 58A, 58B in each of the depressions 54.

After the pattern of the two different silanes 58A, 58B is generated, the orthogonal polymers 10A, 10B are simultaneously applied. Simultaneous deposition of the orthogonal polymers 10A, 10B may involve any suitable deposition technique that can apply both polymers 10A, 10B at the same time. Due to the functionality of the two different silanes 58A, 58B and the functional group pair of the orthogonal polymers 10A, 10B, the orthogonal polymers 10A, 10B are able to selectively attach to the respective silanes 58A, 58B. Thus, the orthogonal polymer 10A attaches to the silane 58A and the orthogonal polymer 10B attaches to the silane 58B. This is shown in FIG. 5F.

In FIG. 5G, the orthogonal polymer 10A that is attached to the silane 58A over the interstitial regions 56 is removed, e.g., using a polishing process as described in reference to FIG. 4G.

As shown in FIG. 5H, the primer sets 12, 14, or 30A, 32A, or 30B, 32B, or 30C, 32C, or 30D, 32D are simultaneously grafted to the respective orthogonal polymers 10A, 10B. Simultaneous grafting of the primer sets 12, 14, or 30A, 32A, or 30B, 32B, or 30C, 32C, or 30D, 32D may involve flow through deposition (e.g., using a temporarily bound lid), dunk coating, spray coating, puddle dispensing, or by another suitable grafting method. Each of these example techniques may utilize a primer solution or mixture, which may include the primer(s) 16, 18, 20, 22 or 34, 36, 38, 40, or 34', 36', 38', 40', water, a buffer, and a catalyst. With any of the grafting methods, the primers 16, 18, or 34, 36, or 34', 36' attach to the orthogonal polymer 10A and have no affinity for the orthogonal polymer 10B or the interstitial regions 56; and the primers 20, 22 or 38, 40, or 38', 40' attach to the orthogonal polymer 10B and have no affinity for the orthogonal polymer 10A or the interstitial regions 56. The selective affinity is due to the functionality of the two different primer sets 12, 14, or 30A, 32A, or 30B, 32B, or 30C, 32C, or 30D, 32D and the functional group pair of the orthogonal polymers 10A, 10B.

Referring now to FIG. 6, another example method is depicted. The method 100 shown in FIG. 6 includes grafting a first primer set 12, or 30A, or 30B, or 30C, or 30D to a first polymer 10A to generate a first pre-grafted polymer (reference numeral 102); grafting a second primer set 14, or 32A, or 32B, or 32C, or 32D to a second polymer 10B to generate a second pre-grafted polymer, wherein the first primer set 12, or 30A, or 30B, or 30C, or 30D is different from the second primer set 14, or 32A, or 32B, or 32C, or 32D and the first polymer 10A is different from the second polymer 10B (reference numeral 104); generating a pattern of two different silanes 58A, 58B on at least a portion of a surface of a substrate 53 (reference numeral 106); and depositing the first and second pre-grafted polymers, whereby the first pre-grafted polymer attaches to a first of the two different silanes and the second pre-grafted polymer attaches to a second of the two different silanes (reference numeral 108).

The first and second polymers in these examples may be any of the orthogonal polymers 10A, 10B disclosed herein. To pre-graft the polymers 10A, 10B, the respective polymers 10A, 10B may be mixed with the respective primer sets 12, 14, or 30A, 32A, or 30B, 32B, or 30C, 32C, or 30D, 32D and exposed to suitable grafting conditions for the reactions that are taking place, e.g., an activated ester functional group of the first orthogonal polymer 10A binding to an amine-terminated primer, or a tetrazine functional group of the second orthogonal polymer 10B binding to a BCN- or norbornene-terminated primer, etc.

The generation of the pattern of the two different silanes 58A, 58B on at least a portion of a surface of a substrate 53 (e.g., in each depression 54) may be accomplished as described in reference to FIG. 4A through FIG. 4E or to FIG. 5A through FIG. 5E.

In one example of the method shown in FIG. 6, the first and second pre-grafted polymers are deposited simultaneously on the substrate 53 (with the pattern of the two different silanes 58A, 58B in each depression). Simultaneous deposition of the pre-grafted orthogonal polymers may involve any suitable deposition technique that can apply both polymers at the same time. Due to the functionality of the two different silanes 58A, 58B and the functional group pair of the pre-grafted orthogonal polymers, the pre-grafted orthogonal polymers are able to selectively attach to the respective silanes 58A, 58B.

In another example of the method shown in FIG. 6, the first and second pre-grafted polymers are deposited sequentially. Due to the functionality of the two different silanes 58A, 58B and the functional group pair of the pre-grafted orthogonal polymers, the first pre-grafted polymer can selectively attach to the silane 58A without having any affinity for the silane 58B and the second pre-grafted polymer can selectively attach to the silane 58B without having any affinity for the silane 58A.

Methods for Using the Flow Cells

Examples of the flow cell 50 disclosed herein including the primer sets 12, 14 attached to the orthogonal polymers 10A, 10B may be used in a sequential paired-end read sequencing method. In this method, the respective forward strands that are generated on each orthogonal polymer 10A, 10B are sequenced and removed, and then the respective reverse strands are sequenced and removed.

Examples of the flow cell 50 disclosed herein including the primer sets 30A, 32A, or 30B, 32B, or 30C, 32C, or 30D, 32D attached to the orthogonal polymers 10A, 10B may be used in a simultaneously paired-end read sequencing method. As described herein, the primer sets 30A, 32A, or 30B, 32B, or 30C, 32C, or 30D, 32D are controlled so that the cleaving (linearization) chemistry is orthogonal at the different polymers 10A, 10B. This enables a cluster of forward strands to be generated in one region (e.g., at orthogonal polymer 10A) of the substrate 53 and a cluster of reverse strands to be generated in another region (e.g., at orthogonal polymer 10B) of the substrate 53. In an example, the regions are directly adjacent to one another within a depression 54 (as shown in FIG. 3B and FIG. 3C). This enables simultaneous paired-end reads to be obtained.

To further illustrate the present disclosure, an example is given herein. It is to be understood that this example is provided for illustrative purposes and is not to be construed as limiting the scope of the present disclosure.

Non-Limiting Working Example

Two different activated ester polymers were synthesized.

The first activated ester polymer was a multi-arm copolymer formed with the following monomers: pentafluorophenyl acrylate and 4-acryloylmorpholine at a ratio of 25:75. The RAFT polymerization took place in the presence of a dendritic RAFT agent (including pentaerythritol as the central molecule and 2-(dodecylthiocarbonothioylthio)-2-methylpropionic acid in each of the 4 arms). AIBN was used as the radical initiator and dioxane was used as the solvent under typical RAFT polymerization conditions, including an argon blanket and 75° C. The NMR results (not reproduced herein) indicate that the polymerization of the monomer reached 60% conversion after 16 hours.

The second activated ester polymer was a linear copolymer formed with pentafluorophenyl acrylate and polydimethylacrylamide methylpropionic acid dodecyltrithiocarbonate (i.e., poly(N,N-dimethylacrylamide), DDMAT terminated, which includes dimethylacrylamide) as the RAFT agent. AIBN was used as the radical initiator and dioxane was used as the solvent under typical RAFT polymerization conditions, including 70° C. for 3 hours. The NMR results (not reproduced herein) indicate that the polymerization of the two monomers reached 35% conversion after 3 hours.

The first (multi-arm) and second (linear) polymers were coated on separate non-patterned HISEQ™ flow cells having APTMS at the surface. The activated esters within each of the two polymers were able to attach to the amino groups at the surface of the flow cell.

The polymer coated flow cells were grafted with amine terminated P5 and P7 oligonucleotide primers. Stress conditions were applied to the grafted polymer coated flow cells that mimic the biochemistry conditions of clustering and sequencing.

After application of the stress conditions, a CFR assay was performed to determine whether grafting of the primers was successful and whether the grafted primers were robust. During the CFR assay, primer grafted surfaces were exposed to fluorescently tagged (CAL FLUOR® Red (CFR) dye) complementary oligonucleotides in a buffer solution. Some of these fluorescently tagged complementary oligonucleotides became bound to surface bound primers and excess CFR tagged complementary oligonucleotides were washed off. The surface was then scanned in a fluorescent detector to measure CFR intensity on the surface to provide a quantitative measure of primers' concentration and health on the surface.

The CFR assay results, i.e., the average measured intensity from the grafted polymer coated flow cells, are shown in FIG. 7. Both materials sufficiently grafted the fluorescently tagged complementary oligonucleotides, indicating that the amine terminated P5 and P7 oligonucleotide primers were attached to each of the linear polymer and the multi-arm polymer coated flow cells.

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

While several examples have been described in detail, it is to be understood that the disclosed examples may be modified. Therefore, the foregoing description is to be considered non-limiting.

What is claimed is:

1. A flow cell, comprising:
a substrate;
a pattern of two different silanes on at least a portion of a surface of the substrate;
a first polymer attached to a first of the two different silanes;
a second polymer attached to a second of the two different silanes, the first and second polymers respectively including a first functional group and a second functional group of a functional group pair, the functional group pair being selected from the group consisting of an activated ester functional group and an azide functional group, a tetrazine functional group and an activated ester functional group, and a tetrazine functional group and an azide functional group;
a first primer set grafted to the first polymer; and
a second primer set grafted to the second polymer, wherein the first and second primer sets are different.

2. The flow cell as defined in claim 1, wherein:
the first polymer is a first homopolymer and the first functional group is the activated ester functional group; and
the second polymer is a second homopolymer and the second functional group is the azide functional group.

3. The flow cell as defined in claim 1, wherein:
the first polymer is a first homopolymer and the first functional group is the tetrazine functional group; and
the second polymer is a second homopolymer and the second functional group is the activated ester functional group.

4. The flow cell as defined in claim 1, wherein:
the first polymer is a first homopolymer and the first functional group is the tetrazine functional group; and
the second polymer is a second homopolymer and the second functional group is the azide functional group.

5. The flow cell as defined in claim 1, wherein:
the first polymer is a first copolymer, the first functional group is the tetrazine functional group, and the first copolymer further includes an additional functional group that includes an azide; and
the second polymer is a second copolymer, the second functional group is the activated ester functional group, and the second copolymer further includes an additional functional group that includes an aryl-iodide.

6. The flow cell as defined in claim 1, wherein:
the first polymer is a first copolymer, the first functional group is the azide functional group, and the first copolymer further includes an additional functional group that includes an acrylamide; and
the second polymer is a second copolymer, the second functional group is the activated ester functional group, and the second copolymer further includes an additional functional group that includes an acrylamide.

7. The flow cell as defined in claim 1, wherein:
the first polymer is a first terpolymer, the first functional group is the tetrazine functional group, and the first terpolymer further includes two additional functional groups that include an azide and an acrylamide; and
the second polymer is a second terpolymer, the second functional group is the activated ester functional group, and the second terpolymer includes two additional functional groups that include an aryl-iodide and an acrylamide.

8. The flow cell as defined in claim 1 wherein the two different silanes are selected from the group consisting of an amino silane and an alkynyl silane, a norbornene silane and an amino silane, and a norbornene silane and an alkynyl silane.

* * * * *